United States Patent
Kim et al.

(10) Patent No.: US 11,938,239 B2
(45) Date of Patent: *Mar. 26, 2024

(54) STERILIZING APPARATUS

(71) Applicant: SEOUL VIOSYS CO., LTD., Ansan-si (KR)

(72) Inventors: Jong Rack Kim, Ansan-si (KR); Hee Cheul Jung, Ansan-si (KR); Sang Wook Jung, Ansan-si (KR); Hee Ho Bae, Ansan-si (KR); Seong Heon Kim, Ansan-si (KR)

(73) Assignee: SEOUL VIOSYS CO., LTD., Ansan-si (KR)

(*) Notice: Subject to any disclaimer, the term of this patent is extended or adjusted under 35 U.S.C. 154(b) by 416 days.

This patent is subject to a terminal disclaimer.

(21) Appl. No.: 17/243,290

(22) Filed: Apr. 28, 2021

(65) Prior Publication Data

US 2021/0244838 A1 Aug. 12, 2021

Related U.S. Application Data

(63) Continuation of application No. 16/734,929, filed on Jan. 6, 2020, now Pat. No. 11,027,033, which is a (Continued)

(30) Foreign Application Priority Data

Jun. 26, 2015 (KR) .................. 10-2015-0091036
Jun. 30, 2015 (KR) .................. 10-2015-0093744
Mar. 3, 2016 (KR) .................. 10-2016-0025592

(51) Int. Cl.
*A61L 2/10* (2006.01)
*A61L 2/26* (2006.01)
(Continued)

(52) U.S. Cl.
CPC ........ *A61L 2/10* (2013.01); *A61L 2/26* (2013.01); *E03C 1/126* (2013.01); *G01B 5/24* (2013.01);
(Continued)

(58) Field of Classification Search
CPC .......... A61L 2/10; A61L 2/26; A61L 2202/11; A61L 2202/121; A61L 2202/122;
(Continued)

(56) References Cited

U.S. PATENT DOCUMENTS 3,998,590 A 12/1976 Glorieux
6,585,392 B2 7/2003 Shiau et al.
(Continued)

FOREIGN PATENT DOCUMENTS

CN 102216826 A 10/2011
CN 102824652 A 12/2012
(Continued)

OTHER PUBLICATIONS

English translation of Korean Office Action from Korean Application No. 10-2015-0093744 dated Dec. 16, 2021 (7 pages).
(Continued)

*Primary Examiner* — Nicole M Ippolito
(74) *Attorney, Agent, or Firm* — Perkins Coie LLP

(57) ABSTRACT

A sterilizing apparatus is disclosed. A sterilizing apparatus according to one embodiment comprises: a cover main body unit having an accommodation space formed therein so as to accommodate a device to be sterilized, wherein the accommodation space is open toward a bottom surface on which the device to be sterilized is disposed; an ultraviolet light emitting diode provided on a surface facing the bottom surface of the cover main body unit, and turned on so as to emit ultraviolet rays toward the accommodation space; a power supply unit for supplying power to the ultraviolet light emitting diode so as to turn on the ultraviolet light
(Continued)

emitting diode; and a control unit for controlling an operation of the power supply unit.

20 Claims, 29 Drawing Sheets

Related U.S. Application Data continuation of application No. 15/854,647, filed on Dec. 26, 2017, now Pat. No. 10,525,153, which is a continuation of application No. PCT/KR2016/006386, filed on Jun. 16, 2016.

(51) Int. Cl.
 *E03C 1/126* (2006.01)
 *G01B 5/24* (2006.01)
 *G01B 11/02* (2006.01)

(52) U.S. Cl.
 CPC ........... *G01B 11/02* (2013.01); *A61L 2202/11* (2013.01); *A61L 2202/121* (2013.01); *A61L 2202/122* (2013.01); *A61L 2202/14* (2013.01); *A61L 2202/17* (2013.01)

(58) Field of Classification Search
 CPC .. A61L 2202/14; A61L 2202/17; E03C 1/126; G01B 5/24; G01B 11/02
 USPC .......................... 250/453.11, 454.11, 455.11
 See application file for complete search history.

(56) References Cited

U.S. PATENT DOCUMENTS

| | | | |
|---|---|---|---|
| 6,753,537 B2 | 6/2004 | Woo | |
| 9,022,035 B2 | 5/2015 | Asada et al. | |
| 9,279,746 B2 | 3/2016 | Wynn | |
| 9,518,720 B2 | 12/2016 | Kim | |
| 9,758,953 B2 | 9/2017 | Bayley et al. | |
| 10,525,153 B2 * | 1/2020 | Kim | G01B 5/24 |
| 11,027,033 B2 * | 6/2021 | Kim | G01B 5/24 |
| 2011/0306213 A1 | 12/2011 | Wang et al. | |

FOREIGN PATENT DOCUMENTS

| | | |
|---|---|---|
| CN | 204387867 U | 6/2015 |
| JP | 2003-501148 A | 1/2003 |
| JP | 2004-41222 A | 2/2004 |
| JP | 2010-275748 A | 12/2010 |
| JP | 2010275748 A | 12/2010 |
| JP | 2013110411 A | 12/2010 |
| JP | 2014133007 A | 7/2014 |
| KR | 20-0335685 Y | 12/2003 |
| KR | 20-0335685 Y1 | 12/2003 |
| KR | 10-0825568 B1 | 4/2008 |
| KR | 10-2010-0042334 A | 4/2010 |
| KR | 10-2011-0085294 A | 7/2011 |
| KR | 10-1145418 B1 | 5/2012 |
| KR | 10-2012-0092465 A | 8/2012 |
| KR | 10-1262661 B1 | 5/2013 |
| KR | 20-2013-0002604 U | 5/2013 |

OTHER PUBLICATIONS

English translation of European Office Action(s) from related European Patent Application No. 16814619.9 dated May 24, 2022 (6 pages).
Supplementary European Search Report from related European Patent Application No. EP16814619 dated Jan. 18, 2019 (12 pages).
English translation of Japanese Office Action from related Japanese Patent Application No. 2017-566777 dated Apr. 21, 2020 (7 pages).
English translation of Chinese Office Action(s) from related Chinese Patent Application No. 201680037592.1 (Aug. 2020) (23 pages).
English translation of Office Action from related Japanese Patent Application No. 2022-109315 dated Jul. 11, 2023 (8 pages).

* cited by examiner

STERILIZING APPARATUS

CROSS-REFERENCE TO RELATED APPLICATIONS

This application is a continuation of U.S. patent application Ser. No. 16/734,929, filed on Jan. 6, 2020, which is a continuation of U.S. patent application Ser. No. 15/854,647, filed on Dec. 26, 2017, which is a continuation of International Application No. PCT/KR2016/006386, filed on Jun. 16, 2016, which claims priority to and the benefit of Korean Patent Application No. 10-2015-0091036, filed on Jun. 26, 2015, and Korean Patent Application No. 10-2015-0093744, filed on Jun. 30, 2015, and Korean Patent Application No. 10-2016-0025592, filed on Mar. 3, 2016, all of which are hereby incorporated by reference for all purposes as if fully set forth herein.

BACKGROUND

Technical Field

The present invention relates to a sterilizing apparatus using a UV light emitting diode to perform sterilization by emitting UV light towards a sterilization target region.

Discussion of the Background

Generally, since various kinds of small devices used in contact with the human body, such as earphones, nail clippers, razors, and mobile phones, are stored in various places for user convenience, such as pockets, bags, the interior of vehicles, and the like, such small devices are likely to contact many kinds of bacteria living in such places and are always exposed to air and an environment into which bacteria floating in the air can be easily introduced.

Therefore, although it is necessary to remove bacteria present in such small devices used in contact with the human body, it is very troublesome and, often, impossible to clean such small devices every time using a detergent.

In addition, a sink drain provides a good environment for bacteria and microorganisms to reproduce. Therefore, if food is not frequently removed from the sink drain and disinfection of the bacteria and microorganisms is not frequently performed, the bacteria and microorganisms will soon reproduce.

Although chemicals capable of suppressing propagation of bacteria and microorganisms have been released in the art in order to prevent an unclean environment of the sink drain, such chemicals cause environmental pollution. Moreover, since the chemicals are frequently washed off by water, it is necessary to frequently replace or replenish the chemicals.

SUMMARY

Exemplary embodiments of the present invention provide a sterilizing apparatus capable of easily and quickly removing bacteria on various kinds of small devices, such as earphones, nail clippers, razors, and mobile phones, at home.

Exemplary embodiments of the present invention provide a drain cap capable of easily and quickly removing bacteria from a drain basin and a filter in a kitchen sink at home and having an ultraviolet sterilizing function.

Exemplary embodiments of the present invention provide a sterilizing apparatus having a simple and reliable waterproof structure and a UV-transmissive window protection structure.

Exemplary embodiments of the present invention provide a sterilizing apparatus capable of securing a sterilization region as much as possible and having high sterilizing power.

Exemplary embodiments of the present invention provide a sterilizing apparatus provided with a safety apparatus which prevents UV light from reaching any other space outside a sterilizing region in any case.

Exemplary embodiments of the present invention provide a sterilizing apparatus which can facilitate sterilization for various purposes.

An exemplary embodiment of the present invention provides a sterilizing apparatus including: a cover body having an accommodation space defined therein to receive a sterilization target device, the accommodation space being open towards a bottom surface on which the sterilization target device is placed; a UV light emitting diode disposed at a side of the cover body facing the bottom surface and emitting UV light towards the accommodation space; a power supply supplying power to the UV light emitting diode to turn on the UV light emitting diode; and a controller controlling the power supply.

The sterilizing apparatus may further include a detection unit detecting movement of the cover body, wherein the controller controls the power supply based on a detection result of the detection unit as to movement of the cover body.

The detection unit may include a gyro sensor sensing a location of the cover body, and the controller may determine whether the cover body is moved based on a detection result of the detection unit as to the location of the cover body and may control the power supply to stop power supply to the UV light emitting diode when the cover body is moved away from the bottom surface on which the sterilization target device is placed.

The detection unit may include a photosensor disposed inside the cover body and sensing light, and the controller may determine whether the cover body is moved based on a detection result of the detection unit as to light detection and may control the power supply to stop power supply to the UV light emitting diode when the cover body is moved away from the bottom surface on which the sterilization target device is placed.

The sterilizing apparatus may further include a switch for manipulating operation of the power supply, wherein the controller controls the power supply in response to manipulation of the switch.

The cover body may include a cover plate having a plate shape and a sidewall extending downward from a lower edge of the cover plate facing the bottom surface, and the UV light emitting diode may be disposed on a lower surface of the cover plate to be placed in an interior region of the cover body surrounded by the lower surface of the cover plate and the sidewall.

The sterilizing apparatus may further include a reflector formed on the cover body and reflecting UV light emitted from the UV light emitting diode towards the accommodation space.

The reflector may be formed by coating aluminum onto the interior region of the cover body surrounded by the lower surface of the cover plate and the sidewall.

The sterilizing apparatus may further include a timer for inputting a time for which the power supply supplies power to the UV light emitting diode, wherein the controller may control a power supply time of the power supply depending on a time set by the timer.

The UV light emitting diode may emit UV light having a peak wavelength of 250 nm to 280 nm.

The sterilizing apparatus may further include a visible light emitting diode provided to the cover body and emitting visible light.

The visible light emitting diode may be turned on in association with turning on of the UV light emitting diode.

An exemplary embodiment of the present invention provides a sterilizing apparatus including: a cover body opening or closing a drain hole in which a drain basin and a filter are disposed; a UV light emitting diode disposed at a side of the cover body facing the drain basin and the filter and emitting UV light towards the drain basin and the filter; a power supply supplying power to the UV light emitting diode to turn on the UV light emitting diode; and a controller controlling the power supply.

The sterilizing apparatus may further include a detection unit detecting whether the drain hole is open or closed by the cover body, wherein the controller may control the power supply based on a detection result of the detection unit as to whether the drain hole is open or closed by the cover body.

The detection unit may include a gyro sensor sensing a location of the cover body, and the controller may determine whether the drain hole is open or closed by the cover body based on a detection result of the detection unit as to the location of the cover body and may control the power supply to stop power supply to the UV light emitting diode when the cover body is placed to open the drain hole.

The detection unit may include a photosensor disposed inside the drain hole and sensing light, and the controller may determine whether the drain hole is open or closed by the cover body based on a detection result of the detection unit as to light detection and may control the power supply to stop power supply to the UV light emitting diode when the cover body is placed to open the drain hole.

The sterilizing apparatus may further include a magnet member embedded in the cover body, wherein the detection unit includes a sensor for sensing a magnetic flux of the magnet member, and the controller may determine whether the drain hole is open or closed by the cover body based on a detection result of the detection unit as to the magnetic flux of the magnet member and may control the power supply to stop power supply to the UV light emitting diode when the cover body is placed to open the drain hole.

The sterilizing apparatus may further include a switch for manipulating operation of the power supply, wherein the controller controls the power supply in response to manipulation of the switch.

The sterilizing apparatus may further include a handle for a user to grip the cover body, wherein the switch is disposed on the handle.

The cover body may include a cover plate having a plate shape corresponding to a shape of the drain hole and a sidewall extending downward from a lower edge of the cover plate facing the drain basin and the filter, and the UV light emitting diode may be disposed on a lower surface of the cover plate to be placed in an interior region of the cover body surrounded by the lower surface of the cover plate and the sidewall.

The sterilizing apparatus may further include a reflector formed on the cover body and reflecting UV light emitted from the UV light emitting diode towards the drain basin and the filter.

The reflector may be formed by coating aluminum onto the interior region of the cover body surrounded by the lower surface of the cover plate and the sidewall.

At least one of the cover body and the sidewall may be formed with an air flow hole through which the interior region of the cover body surrounded by the lower surface and the side wall of the cover plate communicates with an outside of the drain hole.

The sterilizing apparatus may further include a timer for inputting a time for which the power supply supplies power to the UV light emitting diode, wherein the controller may control a power supply time of the power supply depending on a time set by the timer.

The UV light emitting diode may emit UV light having a peak wavelength of 250 nm to 280 nm.

The sterilizing apparatus may further include a visible light emitting diode provided to the cover body and emitting visible light.

The visible light emitting diode may be turned on in association with turning on of the UV light emitting diode.

An exemplary embodiment of the present invention provides a sterilizing apparatus including: a housing having an outer surface facing a sterilization target region; a cover body coupled to the housing to define a space inside the housing; an irradiation opening formed in the housing; a window member receiving portion disposed on an inner surface of the housing around the irradiation opening; a window member provided to the window member receiving portion; a step portion disposed at an edge of the window member receiving portion; a first O-ring disposed on a portion of the window member and the step portion; a compression member secured to the housing to press the first O-ring and having a hole concentrically aligned with the irradiation opening; and a substrate on which a UV light emitting diode is mounted, the UV light emitting diode being disposed inside the housing and emitting UV light through the hole of the compression member and the irradiation opening.

The step portion may have substantially the same height as the window member received in the window member receiving portion.

The irradiation opening may have an irradiation opening-enlarged portion having a cross-section gradually widening from the inner surface of the housing to an outer surface thereof.

The irradiation opening may have a circular shape and the first O-ring may have an annular shape.

The window member may have a square shape.

The housing may include a first jaw formed on the inner surface thereof and supporting an outer circumferential surface of the first O-ring.

The compression member may be provided with a protruding jaw supporting an inner circumferential surface of the first O-ring.

A leading end of the protruding jaw may be separated from the window member by a predetermined distance.

The first O-ring may be formed of a ductile silicone material having a hardness of less than 30 with reference to a hardness of 0 to 100 and the compression member may have higher hardness than the first O-ring.

The sterilizing apparatus may further include an additional elastic member interposed between the window member and the window member receiving portion.

The sterilizing apparatus may further include a second O-ring fitted into a second O-ring receiving groove disposed outside the first jaw with respect to the irradiation opening, wherein the second O-ring may be pressed by the compression member.

The second O-ring receiving groove may be disposed between the first jaw and a second jaw disposed outside the first jaw with respect to the irradiation opening.

The substrate may be secured to the compression member.

The UV light emitting diode may emit UV light having a peak wavelength of 260 nm to 280 nm.

The sterilizing apparatus may further include a detection unit detecting a location or posture of the sterilizing apparatus.

The detection unit may be placed at a location on the substrate exposed through the irradiation opening and the hole of the compression member and may include an illuminance sensor.

The detection unit may be placed at a location on the substrate exposed through the irradiation opening and the hole of the compression member and may include a distance sensor.

According to exemplary embodiments of the present invention, the sterilizing apparatus can easily, quickly, and effectively remove bacteria present in various types of small devices and sinks through simple on/off operation.

In addition, the sterilizing apparatus according to the exemplary embodiments can be manufactured in a small size and can easily sterilize a small device simply by covering the device placed on a bottom surface to secure easy carriage and use convenience.

Further, the sterilizing apparatus according to the exemplary embodiments allows UV irradiation only when all safety conditions are satisfied, thereby further improving operation efficiency while effectively reducing a risk of occurrence of accidents and UV light leakage.

Further, the sterilizing apparatus according to the exemplary embodiments can realize reliable waterproofing and a breakage prevention function of a fragile part even with a simple structure.

Further, the sterilizing apparatus according to the exemplary embodiments can further improve sterilization efficiency and can enlarge a sterilization area.

Further, the sterilizing apparatus according to the exemplary embodiments can reduce UV exposure to the human body as much as possible.

Further, the sterilizing apparatus according to the exemplary embodiments can be used for various purposes and allow convenient sterilization.

DETAILED DESCRIPTION OF THE EMBODIMENTS

Hereinafter, exemplary embodiments of the present invention will be described in detail with reference to the accompanying drawings. It should be noted that the drawings are not to precise scale and may be exaggerated in thickness of lines or size of components for descriptive convenience and clarity only. In addition, the terms used herein are defined by taking functions of the present invention into account and can be changed according to user or operator custom or intention. Therefore, definition of the terms should be made according to the overall disclosure set forth herein.

Figure 1:
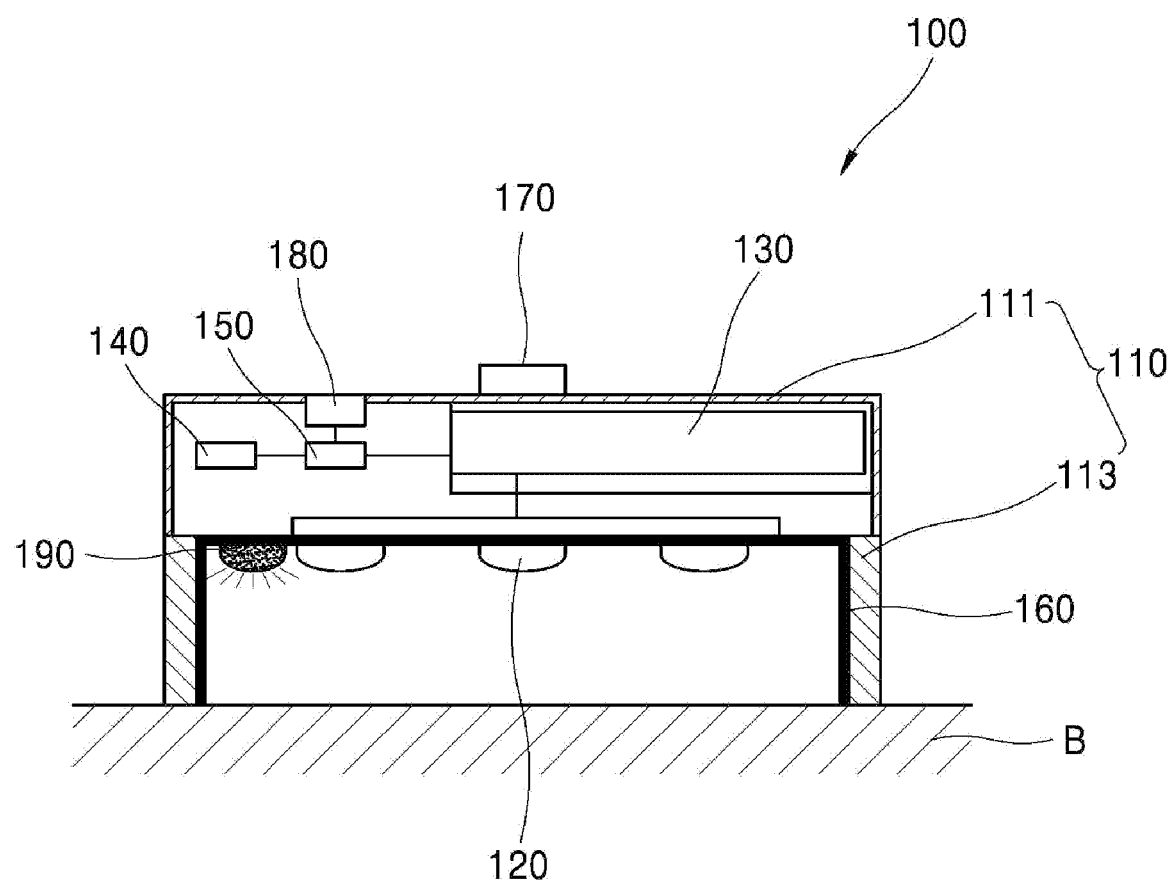
FIG. 1 is a sectional view of a multipurpose sterilizing apparatus according to one embodiment of the present invention.
Figure 2:
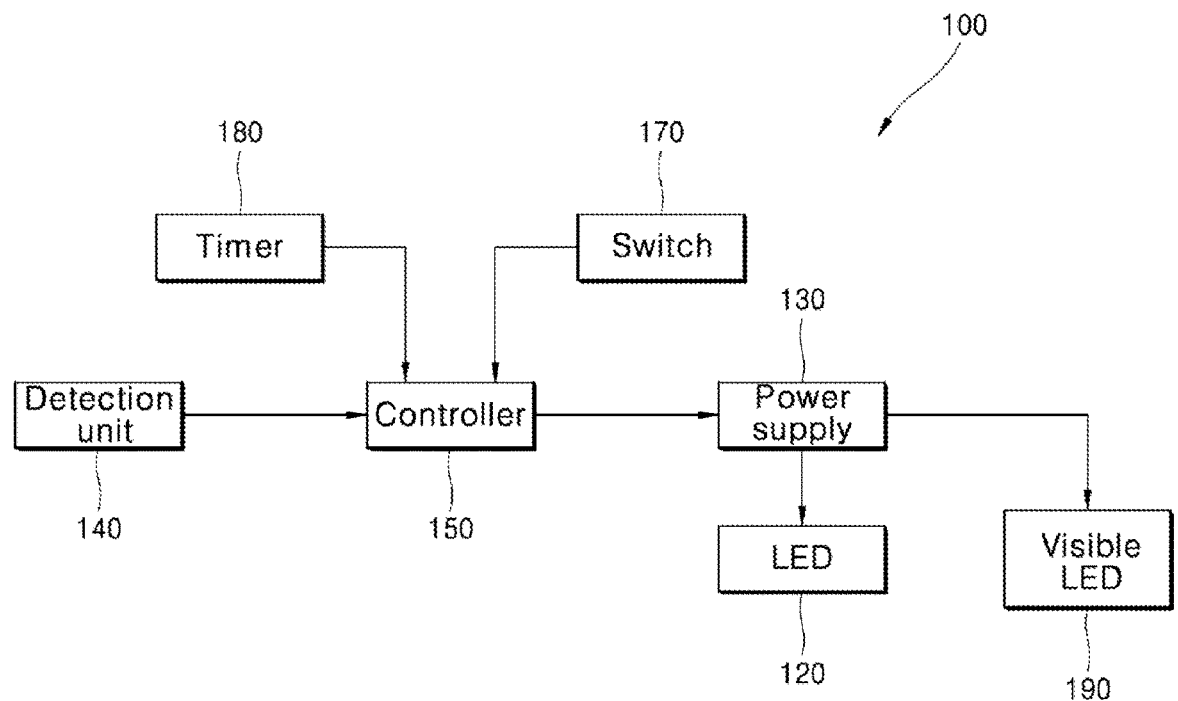
FIG. 2 is a block diagram of the sterilizing apparatus according to the embodiment of the present invention.

FIG. 1 is a sectional view of a sterilizing apparatus according to one embodiment of the present invention and FIG. 2 is a block diagram of the sterilizing apparatus according to the embodiment of the present invention.

Referring to FIGS. 1 and 2, the sterilizing apparatus 100 according to this embodiment may include a cover body 110, a UV light emitting diode 120, a power supply 130, a detection unit 140, and a controller 150.

The cover body 110 constitutes a main body of the sterilizing apparatus 100 and has an accommodation space for a sterilization target 1 (see FIG. 3) therein.

The cover body 110 is formed such that the accommodation space is open toward a bottom surface B on which the sterilization target 1 is placed, and includes a cover plate 111 and a sidewall 113.

The cover plate 111 has a plate shape. Although the cover plate 111 is shown as a rectangular plate in this embodiment, it should be understood that the present invention is not limited thereto and the cover plate 111 may have various shapes such as circular, triangular, and polygonal shapes depending on application thereof.

The sidewall 113 extends downward from an edge of a lower surface of the cover plate 111 facing the bottom surface B.

Thus, the cover body 110 including the cover plate 111 and the sidewall 113 may be placed on the bottom surface B to provide an accommodation space for the sterilization target 1 (FIG. 3) that is optically isolated from the outside.

The UV light emitting diode (LED) 120 is disposed at a side of the cover body 110 facing the bottom surface B and emits UV light toward the accommodation space and the sterilization target 1 received in the accommodation space.

In this embodiment, the UV light emitting diode 120 is disposed on the lower surface of the cover plate 111 to be placed in an interior region of the cover body 110 surrounded by the lower surface of the cover plate 111 and the sidewall 113.

The UV light emitting diode 120 emits UV light having a peak wavelength of 270 nm to 280 nm toward the accommodation space and the sterilization target 1 received in the accommodation space and may include a plurality of UV light emitting diodes such that a surface of the sterilization target 1 received in the accommodation space can be evenly irradiated with UV light.

UV light having a peak wavelength of 270 nm to 280 nm, particularly UV light having a peak wavelength of 275 nm, has high sterilization efficacy.

In this embodiment, the UV light emitting diode 120 is configured to emit UV light having a peak wavelength of 275 nm, thereby enabling active sterilizing action to occur in the accommodation space.

However, in order to provide an efficient level of sterilization, UV light having a peak wavelength in the UVC region, particularly UV light having a peak wavelength of about 250 nm to 280 nm, may be used.

The sterilizing apparatus 100 according to this embodiment may further include a reflector 160.

The reflector 160 is formed on the cover body 110 to reflect UV light from the UV light emitting diode 120 toward the accommodation space and the sterilization target 1 received in the accommodation space.

The reflector 160 may be formed by coating aluminum, which has high UV reflectance, onto an inner surface of the sidewall 113 of the cover body 110 and the lower surface of the cover plate 111 to surround the accommodation space. It should be understood that the reflector 160 may be formed of any suitable material having high UV reflectance as well as aluminum.

Thus, the reflector 160 serves to reflect UV light from the UV light emitting diode 120 toward the accommodation space and the sterilization target 1 received in the accommodation space to focus the UV light on the sterilization target 1 such that the sterilization target 1 can be more effectively sterilized by the UV light.

The power supply 130 supplies electric power to the UV light emitting diode 120 to turn on the UV light emitting diode 120.

The power supply 130 may be realized by a battery disposed inside the cover body 110. Alternatively, the power supply 130 may be realized by an external power source.

The detection unit 140 serves to detect movement of the cover body 110.

If the accommodation space is open to the outside or is not properly closed by the cover body 110, UV light emitted from the UV light emitting diode 120 can escape to the outside of the cover body 110. In order to prevent UV light emitted from the UV light emitting diode 120 from escaping to the outside of the cover body 110, it is necessary to check whether the cover body 110 properly closes the accommodation space.

For this purpose, the detection unit 140 is configured to obtain information about the location of the cover body 110 to check whether the cover body 110 properly closes the accommodation space.

In one example, the detection unit 140 may include a gyro sensor for detecting the location, posture and the like of the cover body 110, without being limited thereto.

In another example, the detection unit 140 may include a photosensor disposed inside the cover body 110. When the cover body 110 covers the bottom surface B such that the accommodation space is surrounded and closed by the cover body 110 and the bottom surface B, the inside of the cover body 110 is darkened. As a result, the detection unit 140 can check whether the cover body 110 properly closes the accommodation space by detecting whether the inside of the cover body 110 is shielded from light.

In a further example, the detection unit 140 may include a plurality of trigger switches protruding from at least two portions of a lower surface of the sidewall 113 to determine closure of the accommodation space inside the cover body 110 depending upon whether the trigger switches are depressed.

In addition, the detection unit 140 may include a combination of the aforementioned examples. For example, in a dark room, the location, posture and the like of the cover body 110 cannot be detected by the photosensor; on an inclined bottom surface, whether the cover body 110 closes the accommodation space cannot be accurately determined using the gyro sensor; and, on an uneven bottom surface, the trigger switches cannot function properly. In order to overcome these problems, the detection unit 140 may include a combination of various sensors as set forth above.

The controller 150 controls operation of the power supply 130 to turn on/off the UV light emitting diode 120. In addition, the controller 150 controls the power supply 130 to be operated depending upon the detection result of the detection unit 140 detecting whether the cover body 110 properly closes the accommodation space.

For example, the controller 150 may determine whether the cover body 110 properly closes the accommodation space based on information about the location and posture of the cover body 110 detected by the detection unit 140. If the cover body 110 is placed to open the accommodation space, the controller 150 may control the power supply 130 such that power supply to the UV light emitting diode 120 can be stopped.

That is, the controller 150 may control the power supply 130 to supply power to the UV light emitting diode 120 so as to turn on the UV light emitting diode 120. In this operation, the controller 150 determines whether the cover body 110 is open or closed based on the information about the location and posture of the cover body 110 detected by the detection unit 140. If it is determined that the cover body 110 opens or does not properly closes the accommodation space, the controller 150 can stop irradiation with UV light through the UV light emitting diode 120 by controlling the power supply 130 to stop power supply to the UV light emitting diode 120.

The sterilizing apparatus 100 according to this embodiment may further include a switch 170.

The switch 170 is provided to control the power supply 130. In this embodiment, the switch 170 is disposed at an upper portion of the cover body 110, more specifically, on an upper surface of the cover plate 111, in order to allow easy manipulation of the switch 170 by a user.

Such a switch 170 may be provided to manipulate on/off operation of the power supply 130 and the controller 150 controls the power supply 130 to be turned on or turned off through manipulation of the switch 170.

The sterilizing apparatus 100 according to this embodiment may further include a timer 180.

The timer 180 is provided as a means for inputting a period of time for which the power supply 130 supplies power to the UV light emitting diode 120, and the controller 150 can control a power supply time of the power supply 130 according to the period of time adjusted by the timer 180.

For example, if the period of time input through the timer 180 is set to 10 minutes, the controller 150 controls the power supply 130 to supply power to the UV light emitting diode 120 such that the UV light emitting diode 120 can be turned off after the UV light emitting diode 120 is turned on to emit UV light for 10 minutes.

The sterilizing apparatus 100 according to this embodiment may further include a visible light emitting diode 190.

The visible light emitting diode 190 is disposed near the UV light emitting diode 120 inside the cover body 110, more specifically in an interior region of the cover body 110 surrounded by the lower surface of the cover plate 111 and the sidewall 113.

With this structure, the visible light emitting diode 190 emits light in the visible range at a location near the UV light emitting diode 120 when the UV light emitting diode 120 is turned on, and is operated in conjunction with the UV light emitting diode 120.

Specifically, the visible light emitting diode 190 is turned on to emit light in the visible range when the UV light emitting diode 120 is turned on to emit UV light, thereby providing a function of displaying UV irradiation through the UV light emitting diode 120.

With such operation of the visible light emitting diode 190, a user can easily recognize that UV light is emitted through the UV light emitting diode 120 and thus can be prevented from being continuously exposed to UV light not perceived by the user during irradiation with the UV light emitted from the UV light emitting diode 120.

Figure 3:
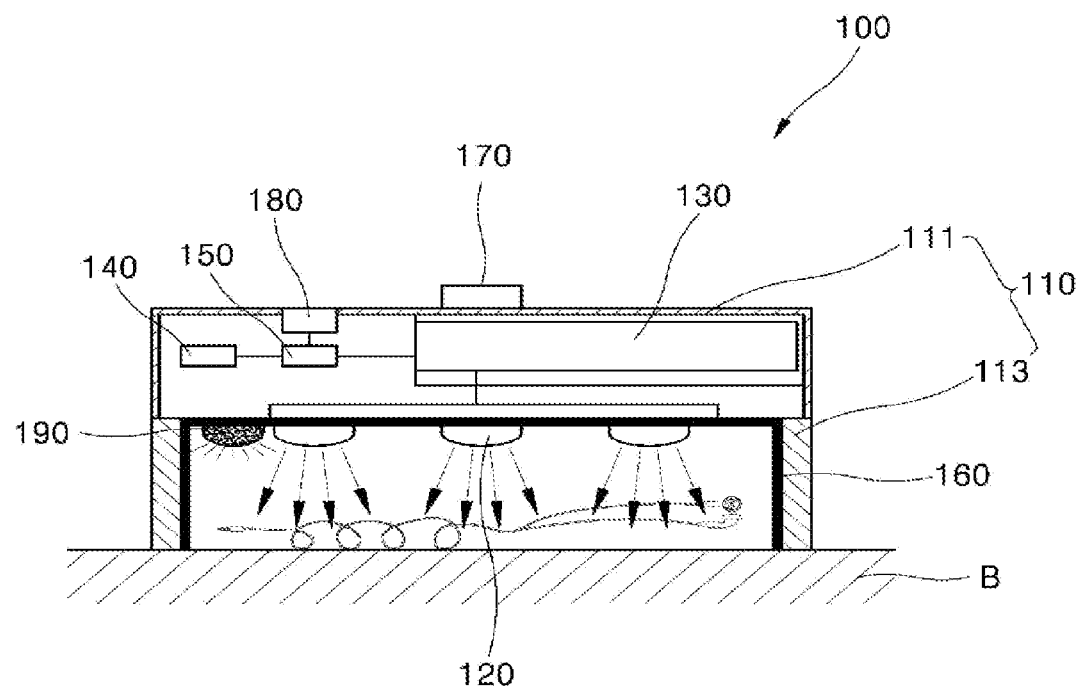
FIG. 3 is a sectional view illustrating one example of use of the portable multipurpose sterilizing apparatus according to the embodiment of the present invention.
Figure 4:
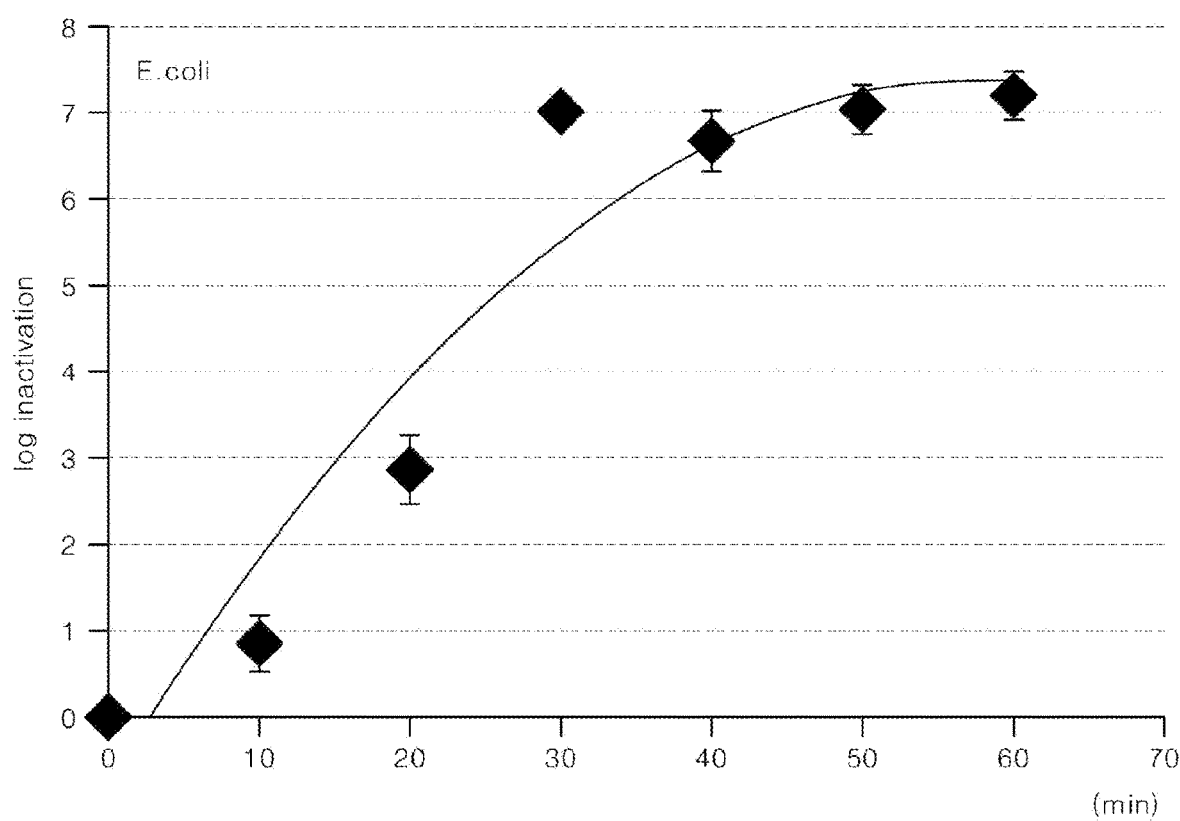
FIG. 4 and FIG. 5 are graphs depicting inactivation levels of E. coli depending upon UV irradiation time and irradiation amount of the portable multipurpose sterilizing apparatus according to the embodiment of the present invention.
Figure 5:
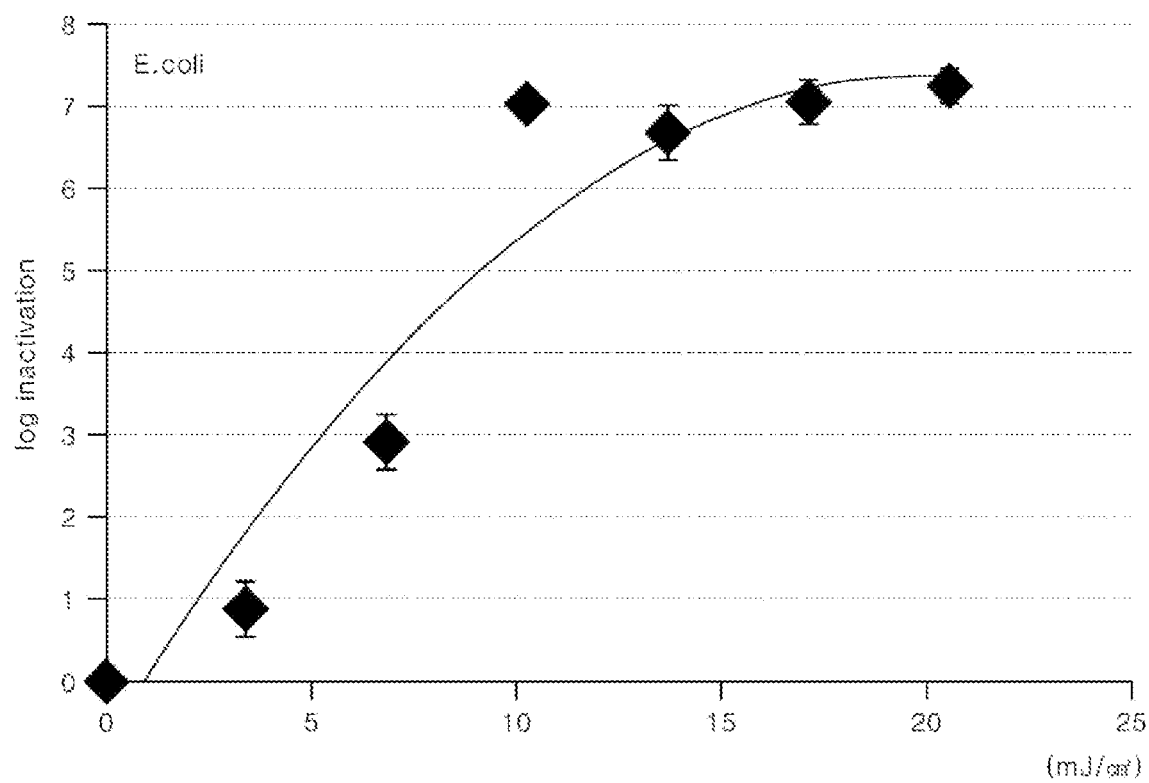
Figure 6:
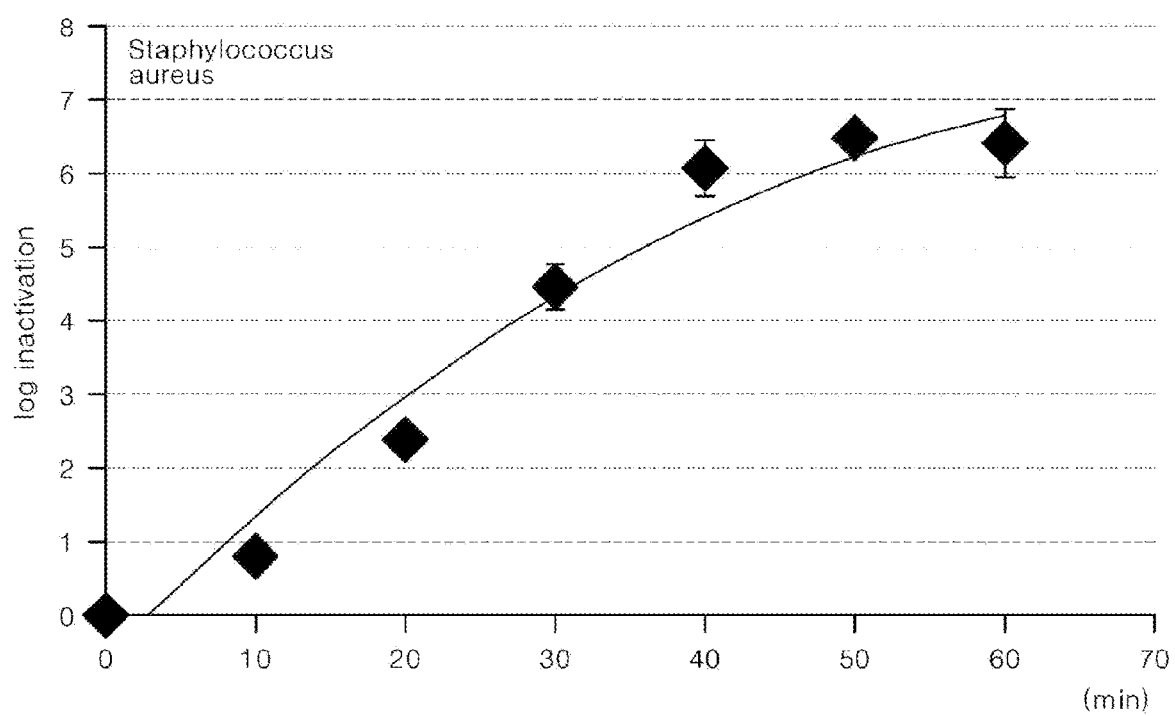
FIG. 6 and FIG. 7 are graphs depicting inactivation levels of Staphylococcus aureus depending upon UV irradiation time and irradiation amount of the portable multipurpose sterilizing apparatus according to the embodiment of the present invention.
Figure 7:
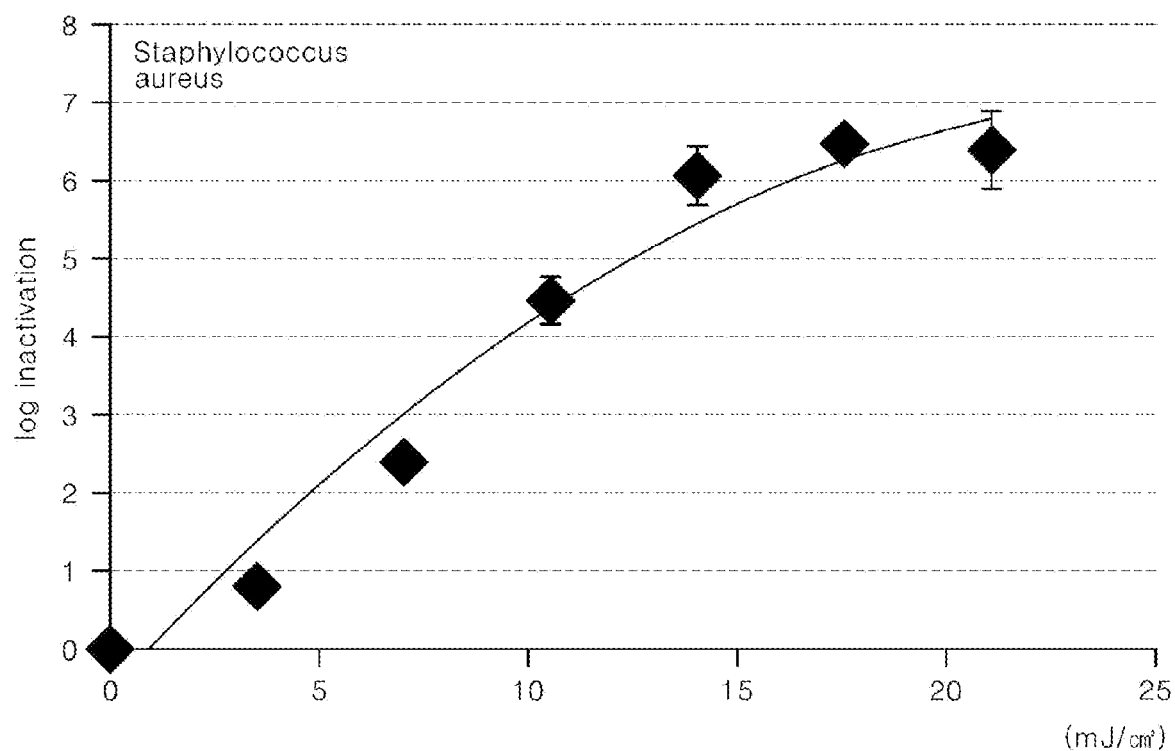

FIG. 3 is a sectional view illustrating one example of use of the portable multipurpose sterilizing apparatus according to the embodiment of the present invention; FIG. 4 and FIG. 5 are graphs depicting inactivation levels of *E. coli* depending upon UV irradiation time and irradiation amount of the portable multipurpose sterilizing apparatus according to the embodiment of the present invention; and FIG. 6 and FIG. 7 are graphs depicting inactivation levels of *Staphylococcus aureus* depending upon UV irradiation time and irradiation amount of the portable multipurpose sterilizing apparatus according to the embodiment of the present invention.

Next, operation and advantageous effects of the sterilizing apparatus according to this embodiment will be described with reference to FIG. 2 to FIG. 7.

Referring to FIG. 2 and FIG. 3, the sterilizing apparatus 100 according to this embodiment sterilizes a sterilizing target device, for example, a small device such as an earphone, a nail clipper, a mobile phone, and the like, disposed on the bottom surface B, with the cover body 110 covering the sterilizing target device so as to be received in the accommodation space thereof, and the sterilizing operation of the sterilizing apparatus 100 is controlled by the controller 150.

The operation of the sterilizing apparatus 100 for sterilizing of the sterilization target device received in the accommodation space can be started by manipulating the switch 170 disposed on the upper surface of the cover body 110.

For example, when the sterilizing target device placed on the bottom surface B is covered with the cover body 110 to be received in the accommodation space and an operation signal is input through the switch 170, the signal is transmitted to the controller 150, which in turn starts to control the power supply 130 in response to the signal.

The detection unit 140 senses the location of the cover body 110 and obtains information about the location and posture of the cover body 110, and the controller 150 determines whether the accommodation space is open or closed by cover body 110, based on the information about the location and posture of the cover body 110.

As a result, if it is determined that the accommodation space is closed by the cover body 110, the controller 150 controls the power supply 130 to supply power to the UV light emitting diode 120, and if it is determined that the accommodation space is open or is not properly closed by the cover body 110, the controller 150 controls the power supply 130 such that power is not supplied to the UV light emitting diode 120.

As such, the operation of the UV light emitting diode 120 is controlled only when the accommodation space is closed by the cover body 110, thereby preventing inefficient operation of the sterilizing apparatus 100, reducing accident risk, and preventing UV light emitted from the UV light emitting diode 120 from leaking to the outside of the cover body 110 and providing a harmful effect on the human body.

In this way, when power is supplied to the UV light emitting diode 120 through operation control of the controller 150, the UV light emitting diode 120 is turned on to emit ultraviolet light toward the sterilization target device.

Here, the UV light emitting diode 120 emits UV light exhibiting strong sterilizing properties, for example, UV light having a peak wavelength in the range of 270 nm to 280 nm, more preferably UV light having a peak wavelength of 275 nm.

In this way, operation of the detection unit 140 is continued during operation of the UV light emitting diode 120, and during this operation, if it is determined that the accommodation space is open or is not properly closed by the cover body 110, based on the information about the location and posture of the cover body 110 obtained by the detection unit 140, the controller 150 controls the power supply 130 to stop power supply to the UV light emitting diode 120, whereby the UV light emitting diode 120 can be turned off to stop UV irradiation.

In addition, the UV light emitting diode 120 may be turned off when the power supply time of the power supply 130 set by the timer 180 has elapsed, and whether the UV light emitting diode 120 is turned on or off can be determined based on whether the visible light emitting diode 190 is turned on or off.

That is, in the sterilizing apparatus 100 according to this embodiment, UV irradiation can be performed only when the operation signal is input through the switch 170 in the state that the accommodation space is closed by the cover body 110; power supply can be automatically interrupted to stop UV irradiation when there is a risk of UV light leakage due to instability of the cover body 110 during operation of the cover body 110 or when a preset period of time has elapsed; and whether the UV light emitting diode 120 is turned on to emit UV light can be determined based on whether the visible light emitting diode 190 is turned on.

The sterilizing apparatus 100 according to this embodiment allows UV irradiation only when the safety conditions described above are satisfied, thereby further improving operation efficiency while effectively reducing accident risk and leakage of UV light.

On the other hand, UV light emitted from the UV light emitting diode 120 is directed to the sterilization target device received in the accommodation space, thereby enabling sterilization on the surface of the sterilizing target device.

According to this embodiment, a plurality of UV light emitting diodes 120 is provided to the sterilizing apparatus such that the entire region of the sterilization target device can be irradiated with UV light, and the reflector 160 is disposed to reflect UV light emitted from the UV light emitting diodes 120 towards the accommodation space and the sterilization target device received in the accommodation space so as to focus the UV light on the sterilization target device, thereby enabling active sterilization over the entire region of the sterilization target device.

As sterilization effects through sterilization using the sterilizing apparatus 100 according to this embodiment described above, it can be seen that inactivation of *E. coli* approached 99.9% on the sterilization target device upon UV irradiation at a dose of about 5 mJ/cm$^2$ for about 15 minutes and most of *E. coli* remaining on the surface of the sterilization target device was sterilized during sterilization through UV irradiation (see FIG. 4 and FIG. 5).

In addition, it can be seen that inactivation of *Staphylococcus aureus* approached 99.9% on the sterilization target device upon UV irradiation at a dose of about 7 mJ/cm$^2$ for about 20 minutes and most of *Staphylococcus aureus* remaining on the surface of the sterilization target device was sterilized during sterilization through UV irradiation (see FIG. 6 and FIG. 7).

The sterilizing apparatus 100 according to this embodiment allows automatic UV sterilization with respect to various kinds of small devices, such as earphones, nail clippers, mobile phones, and the like, through simple on/off operation, so that various bacteria remaining on such small sterilization target devices can be removed with high efficiency, thereby enabling easy, rapid and effective removal of bacteria present on various types of small devices at home.

In addition, since the sterilizing apparatus 100 according to this embodiment can be manufactured in a small size, the sterilizing apparatus 100 according to this embodiment is convenient to carry and provides use convenience through easy sterilization of a small device simply by covering the small device placed on the bottom surface.

Further, the sterilizing apparatus 100 according to this embodiment allows UV irradiation only when various safety conditions, such as operation of the switch 170, detection of the closed state of the accommodation space through the detection unit 140, and operation time setting through the timer 180, are satisfied, thereby further improving operation efficiency of the sterilizing apparatus while effectively reducing accident risk and leakage of UV light.

Figure 8:
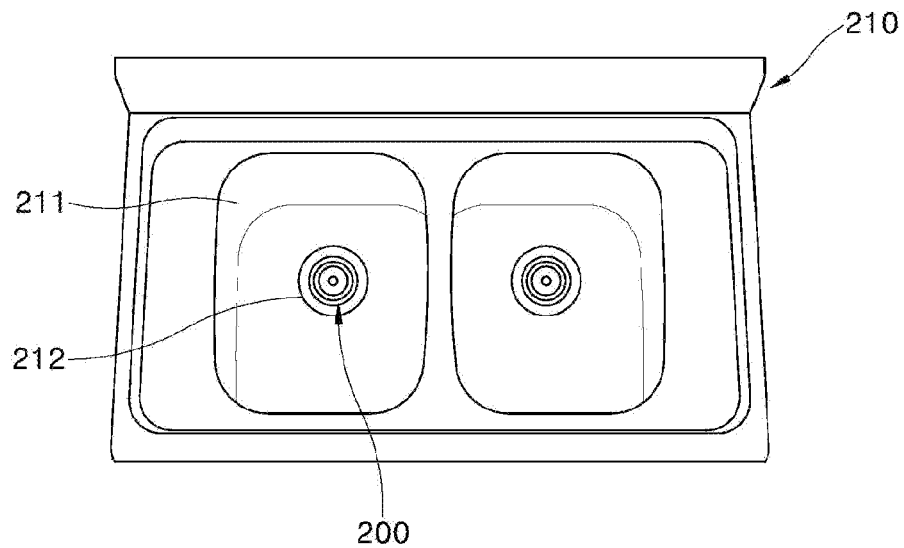
FIG. 8 is a view showing an installation state of a drain cap having a UV sterilizing function according to one embodiment of the present invention.
Figure 9:
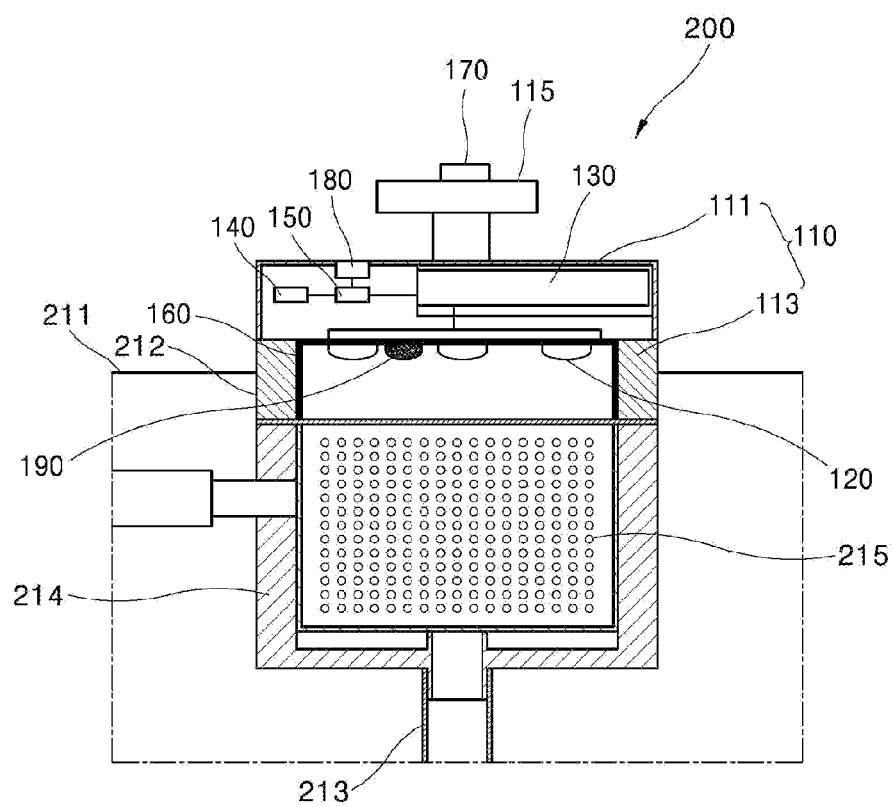
FIG. 9 is a cross-sectional view of the drain cap having a UV sterilizing function according to the embodiment of the present invention.
Figure 10:
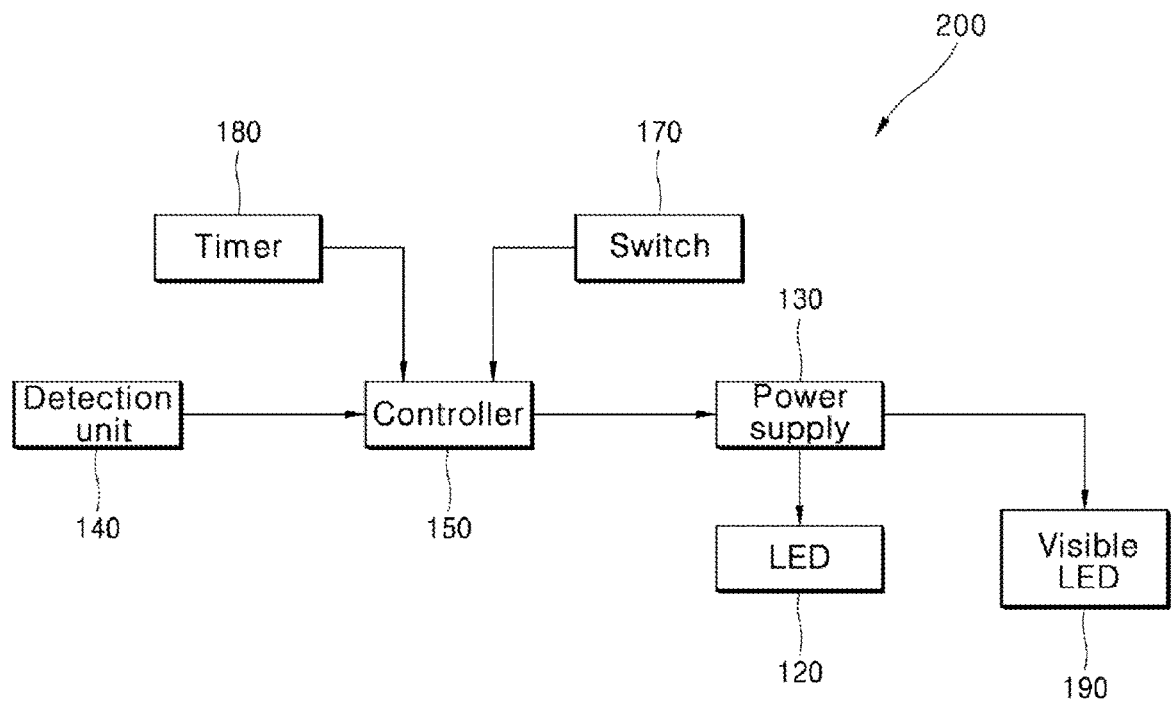
FIG. 10 is a block diagram of the drain cap having a UV sterilizing function according to the embodiment of the present invention.

FIG. 8 is a view showing an installation state of a sterilizing apparatus according to another embodiment of the present invention, FIG. 9 is a cross-sectional view of the drain cap having a UV sterilizing function according to the embodiment of the present invention, and FIG. 10 is a block diagram of the drain cap having a UV sterilizing function according to the embodiment of the present invention.

Referring to FIG. 8 to FIG. 10, a sterilizing apparatus 200 according to another embodiment is provided to a bottom of a wash basin of a sink 210 to open or close a drain hole 212 formed at the bottom of the wash basin 211.

In the drain hole 212, a drain basin 214 is disposed to connect the drain hole 212 to a drainage pipe 213 and is provided with a filter 215 that filters food residues or foreign substances remaining in the sewage discharged through the drain hole 212.

The sterilizing apparatus 200 according to this embodiment is detachably provided to the wash basin 211 to open or close the drain hole 212 above the drain basin 214 and the filter 215, and may include light emitting diodes 120, a power supply 130, a detection unit 140, and a controller 150.

The cover body 110 constitutes a main body of the sterilizing apparatus 200 according to the present embodiment, and opens or closes the drain hole 212, which is provided therein with the drain basin 214 and the filter 215. The cover body 110 includes a cover plate 111 and a sidewall 113.

The cover plate 111 is formed in a plate shape corresponding to the shape of the drain hole 212. In this embodiment, the drain hole 212 has a circular shape and the cover plate 111 has a disk shape corresponding to the shape of the drain hole 212.

The sidewall 113 extends downward from a bottom edge of the cover plate 111 facing the drain basin 214 and the filter 215.

In the cover body 110 including the cover plate 111 and the sidewall 113, the sidewall 113 may be inserted into the drain hole 212, and the cover plate 111 may be coupled to the wash basin 211 to close the drain hole 212 by covering the drain hole 212 and may be separated from the wash basin 211 to open the drain hole 212.

However, the sidewall 113 is not necessarily inserted into the drain hole 212 and may be disposed such that a lower surface of the sidewall 113 is placed on the bottom surface of the wash basin 211.

The sterilizing apparatus 200 according to this embodiment may further include a handle 115.

The handle 115 may protrude from an upper surface of the cover body 110, that is, an upper surface of the cover plate 111, such that a user can grip the cover body 110. Thus, a user can easily open or close the drain hole 212 by grasping the handle 115.

The UV light emitting diodes (LEDs) 120 are disposed at a side of the cover body 110 facing the drain basin 214 and the filter 215, and is turned on to emit UV light towards at least one of the drain basin 214 and the filter 215.

In this embodiment, the UV light emitting diode 120 is disposed on a lower surface of the cover plate 111 so as to be placed inside the cover body 110 surrounded by the lower surface of the cover plate 111 and the sidewall 113.

An air flow hole (not shown) may be formed in at least one of the cover plate 111 and the sidewall 113.

The air flow hole forms a flow channel, through which the interior of the cover body 110 surrounded by the lower surface of the cover plate 111 and the sidewall 113 communicate with the outside of the drain hole 212, such that moisture can be discharged from the drain hole 212 therethrough, thereby suppressing influence of the moisture remaining in the drain basin 214 and the filter 215 on the UV light emitting diode 120.

The UV light emitting diode 120 is disposed to emit UV light having a peak wavelength of 270 nm to 280 nm towards the drain basin 214 and the filter 215, and a plurality of such UV light emitting diodes 120 is arranged at constant intervals to uniformly emit UV light to the entirety of the drain basin 214 and the filter 215.

Among UV light, ultraviolet light having a peak wavelength of 270 nm to 280 nm, particularly UV light having a peak wavelengths of 275 nm, has an excellent sterilizing effect.

In this embodiment, the UV light emitting diode 120 is configured to emit UV light having a peak wavelength of 275 nm and sterilization can be actively performed inside the drainage pipe 213 through operation of the UV light emitting diode 120.

However, in order to obtain an effective level of sterilization effect, UV light in the UVC range, particularly, UV light having a peak wavelength of about 950 nm to 280 nm, may be used.

The sterilizing apparatus 200 according to this embodiment may further include a reflector 160.

The reflector 160 is formed on the cover body 110 to reflect UV light emitted from the UV light emitting diode 120 toward the drain basin 214 and the filter 215.

The reflector 160 may be formed by coating the interior region of the cover body 110 surrounded by the lower surface of the cover plate 111 and the sidewall 113 with aluminum or other coating materials having high reflectivity with respect to UV light.

The reflector 160 reflects UV light emitted from the UV light emitting diode 120 toward the drain basin 214 and the filter 215 to focus UV irradiation on the drain basin 214 and the filter 215, thereby enabling more effective sterilization of the drain basin 214 and the filter 215.

The power supply 130 supplies power to the UV light emitting diode 120 to turn on the UV light emitting diode 120.

The power supply 130 may be realized by a battery disposed inside the cover body 110 to supply power to the UV light emitting diode 120, or may be realized by an external power source that supplies power to the UV light emitting diode 120 through the power supply 130.

The detection unit 140 is disposed to detect whether the drain hole 212 of the cover body 110 is open or closed.

If the cover body 110 opens or does not properly close the drain hole 212, UV light emitted from the UV light emitting diode 120 can leak through the drain hole 212. Thus, in order to prevent UV light emitted from the UV light emitting diode 120 from leaking through the drain hole 212, it is necessary to determine whether the cover body 110 properly closes the drain hole 212.

To this end, the detection unit 140 can obtain information about the location of the cover body 110 in order to determine whether the cover body 110 properly closes the drain hole 212.

In one example, the detection unit 140 may include a gyro-sensor that senses the location, posture, and the like of the cover body 110, without being limited thereto.

In another example, the detection unit 140 may include a photosensitive sensor disposed inside the drain hole 212. When the drain hole 212 is covered by the cover body 110, the interior of the drain hole 212 is darkened. Thus, the detection unit 140 can determine whether the cover body 110 properly closes the drain hole 212 by sensing whether light is blocked inside the drain hole 212.

In a further example, the detection unit 140 may be realized by a magnet member disposed inside the cover body 110 and a sensor disposed inside the drain hole 212 to sense a magnetic flux of the magnet member, or by a sensor provided with a switch that can be pressed when the cover body 110 is covered.

In yet another example, the detection unit 140 may be realized by at least two triggers (not shown) protruding from the lower surface of the sidewall 113 so as to determine whether the drain hole 212 of the cover body 110 is closed depending upon whether the trigger switches are pressed.

The controller 150 controls the power supply 130 such that the UV light emitting diode 120 can be turned on or off. The controller 150 controls the power supply 130 depending upon a detection result of the detection unit 140 as to whether the drain hole 212 of the cover body 110 is open or closed.

By way of example, the controller 150 may determine whether the drain hole 212 of the cover body 110 is open or closed based on information about the location and posture of the cover body 110 detected by the detection unit 140. If the cover body 110 is placed to open the drain hole 212, the controller 150 may control the power supply 130 such that power supply to the UV light emitting diode 120 can be stopped.

That is, the controller 150 may control the power supply 130 to supply power to the UV light emitting diode 120 so as to turn on the UV light emitting diode 120. In this operation, the controller 150 determines whether the drain hole 212 of the cover body 110 is open or closed based on the information about the location and posture of the cover body 110 detected by the detection unit 140. If it is determined that the cover body 110 opens or does not properly close the drain hole 212, the controller 150 can stop irradiation with UV light through the UV light emitting diode 120 by controlling the power supply 130 to stop power supply to the UV light emitting diode 120.

The sterilizing apparatus 200 according to this embodiment may further include a switch 170.

The switch 170 is provided to control the power supply 130. In this embodiment, the switch 170 is provided to the handle 115 in order to allow easy manipulation of the switch 170 by a user.

Such a switch 170 may be provided to manipulate on/off operation of the power supply 130 and the controller 150 controls the power supply 130 to be turned on or turned off through manipulation of the switch 170.

The sterilizing apparatus 200 according to this embodiment may further include a timer 180.

The timer 180 is provided as a means for inputting a period of time for which the power supply 130 supplies power to the UV light emitting diode 120, and the controller 150 can control a power supply time of the power supply 130 according to the period of time adjusted by the timer 180.

For example, if the period of time input through the timer 180 is set to 10 minutes, the controller 150 controls the power supply 130 to supply power to the UV light emitting diode 120 such that the UV light emitting diode 120 can be turned off after the UV light emitting diode 120 is turned on to emit UV light for 10 minutes.

The sterilizing apparatus 200 according to this embodiment may further include a visible light emitting diode 190.

The visible light emitting diode 190 is disposed near the UV light emitting diode 120 inside the cover body 110, more specifically in an interior region of the cover body 110 surrounded by the lower surface of the cover plate 111 and the sidewall 113.

With this structure, the visible light emitting diode 190 emits light in the visible range at a location near the UV light emitting diode 120 when the UV light emitting diode 120 is turned on, and is operated in conjunction with the UV light emitting diode 120.

Specifically, the visible light emitting diode 190 is turned on to emit light in the visible range when the UV light emitting diode 120 is turned on to emit UV light, thereby providing a function of displaying UV irradiation through the UV light emitting diode 120.

With such operation of the visible light emitting diode 190, a user can easily recognize that UV light is emitted through the UV light emitting diode 120 and thus can be prevented from being continuously exposed to UV light not perceived by the user during irradiation with the UV light emitted from the UV light emitting diode 120.

Figure 11:
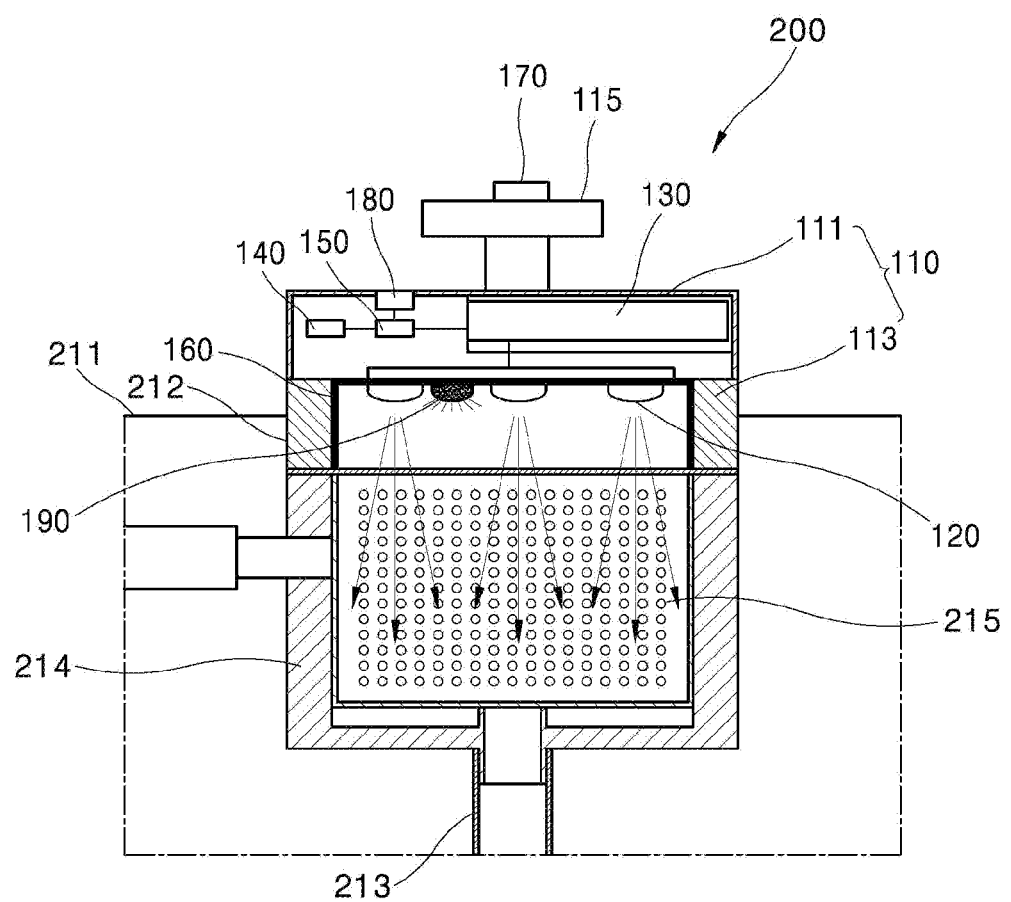
FIG. 11 is a view illustrating one example of use of the drain cap having a UV sterilizing function according to the embodiment of the present invention.
Figure 12:
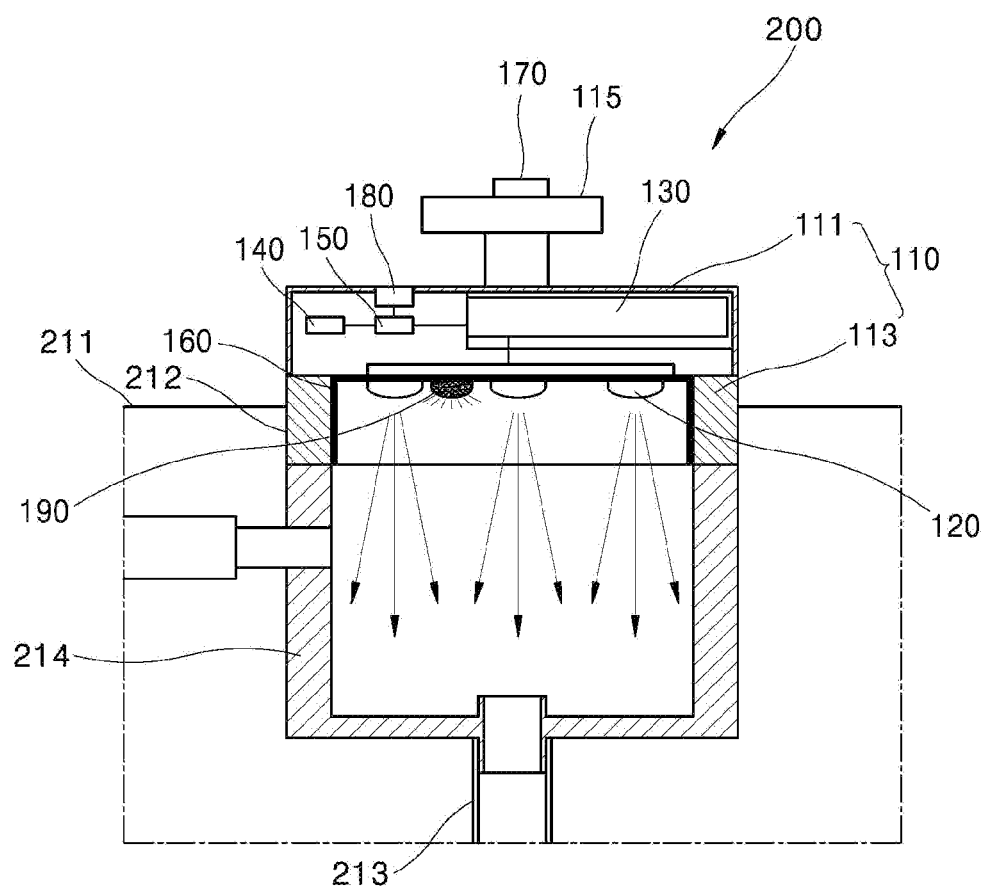
FIG. 12 is a view illustrating another example of use of the drain cap having a UV sterilizing function according to the embodiment of the present invention.
Figure 13:
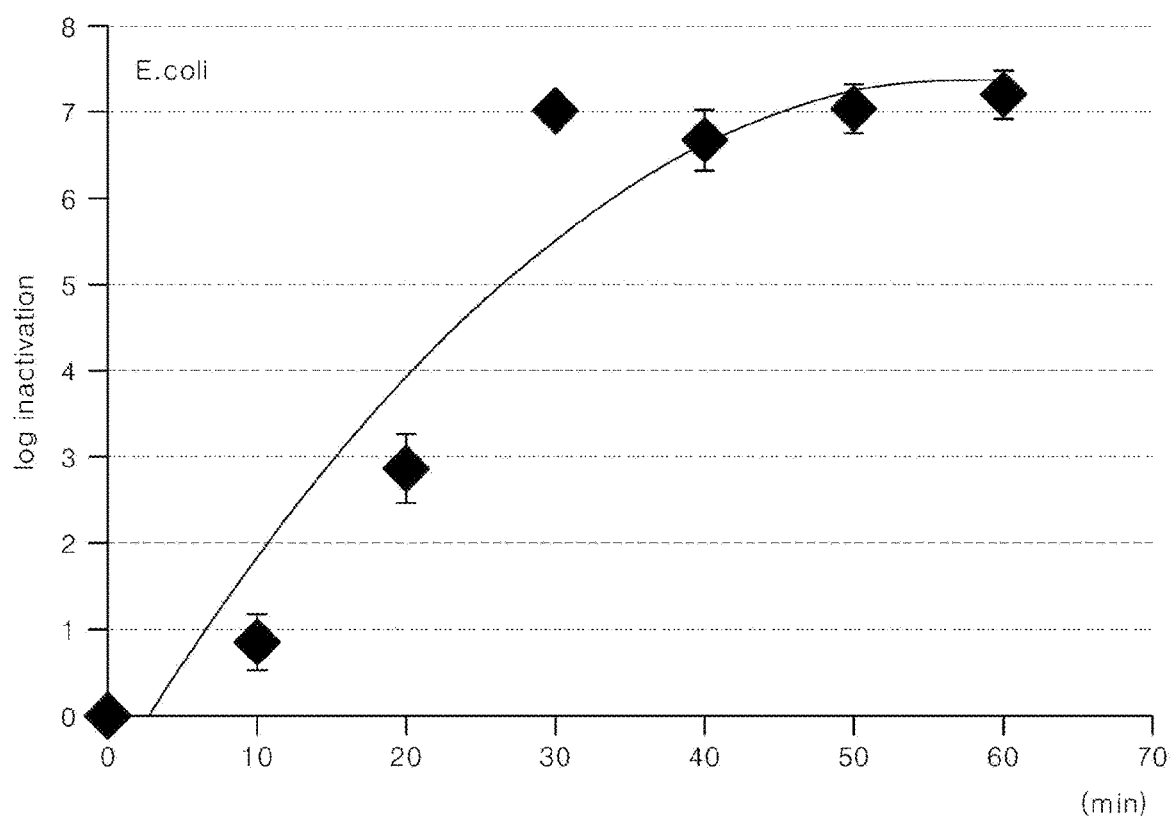
FIG. 13 and FIG. 14 are graphs depicting inactivation levels of E. coli depending upon UV irradiation time and irradiation amount of the drain cap having a UV sterilizing function according to the embodiment of the present invention.
Figure 14:
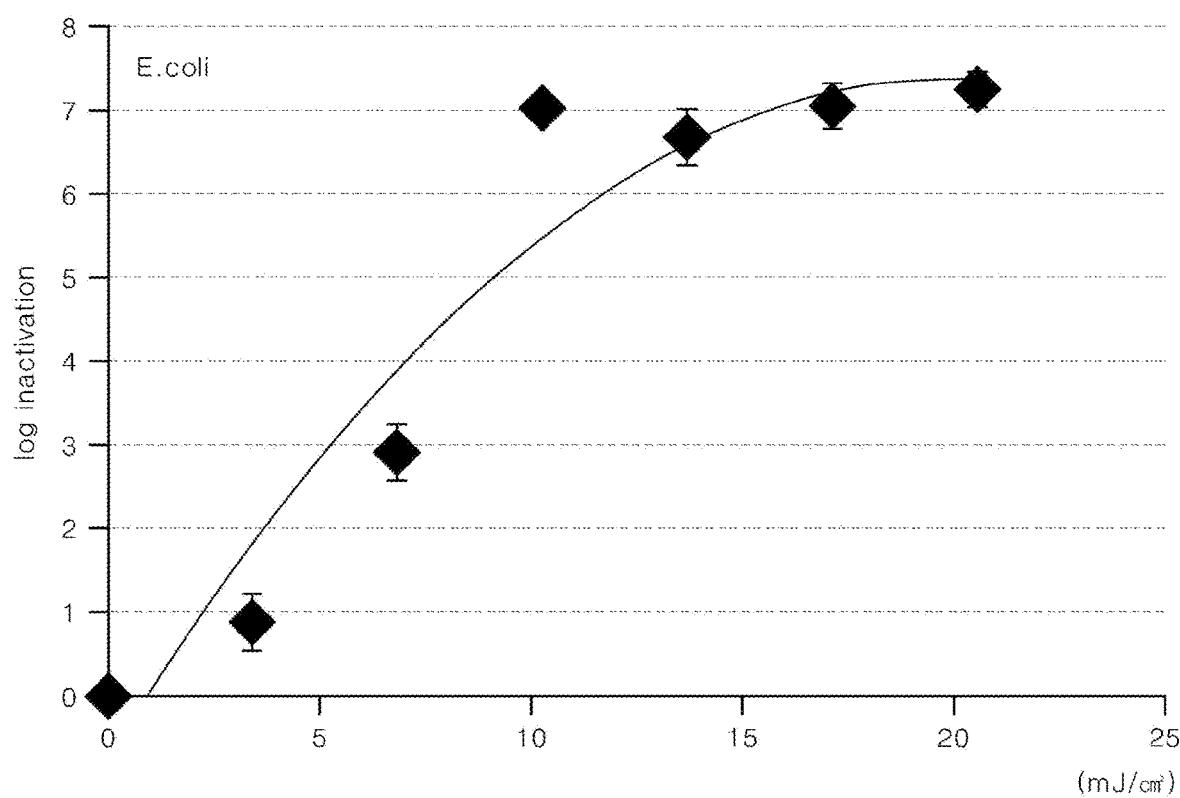
Figure 15:
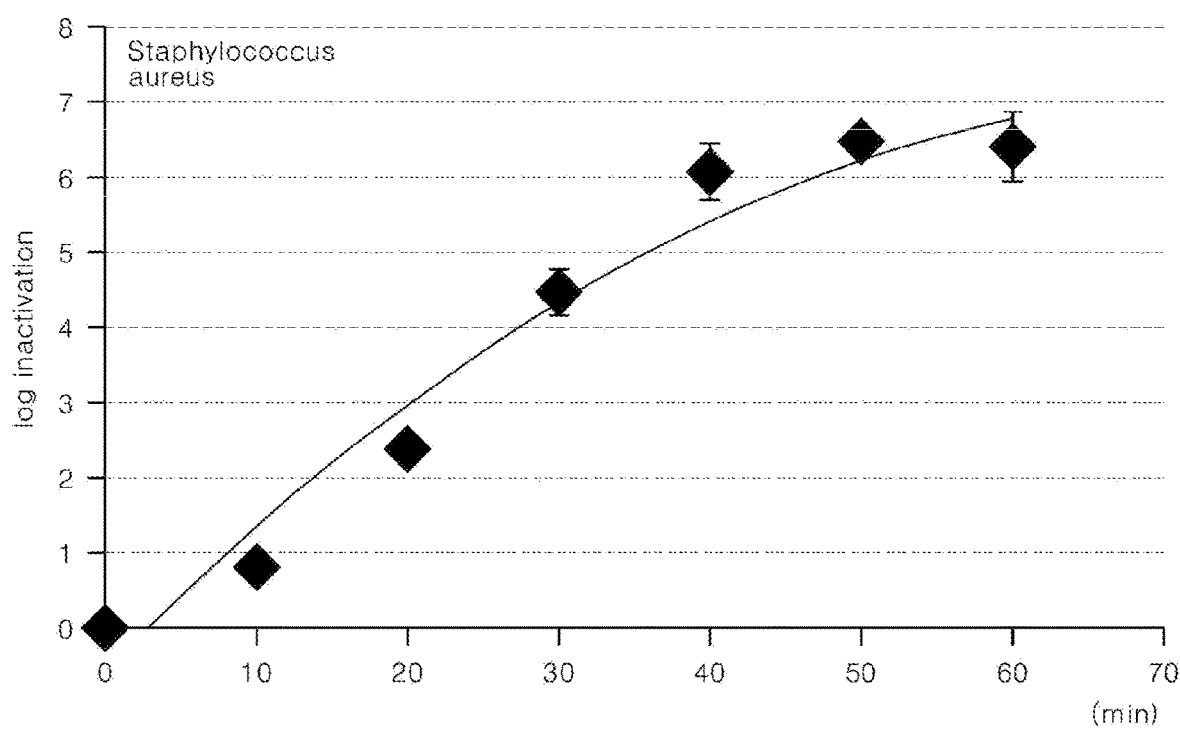
FIG. 15 and FIG. 16 are graphs depicting inactivation levels of Staphylococcus aureus depending upon UV irradiation time and irradiation amount of the drain cap having a UV sterilizing function according to the embodiment of the present invention.
Figure 16:
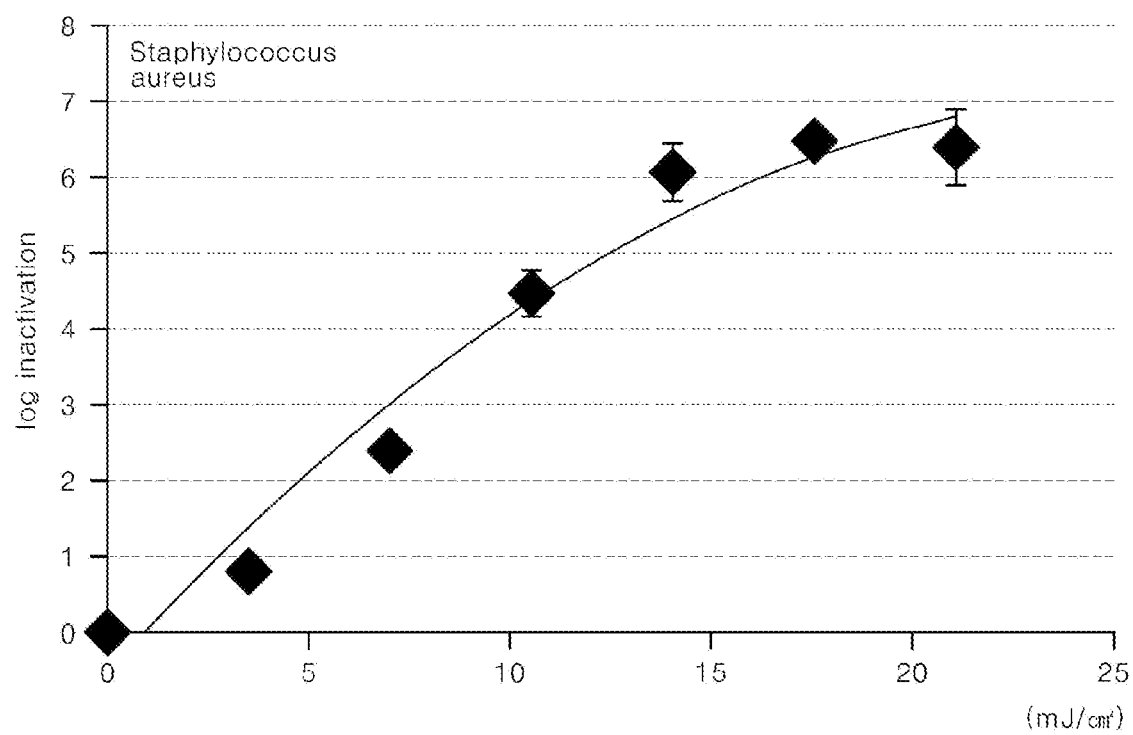

FIG. 11 is a sectional view illustrating one example of use of the sterilizing apparatus according to this embodiment and FIG. 12 is a sectional view illustrating another example of use of the sterilizing apparatus according to this embodiment. In addition, FIG. 13 and FIG. 14 are graphs depicting inactivation levels of *E. coli* depending upon UV irradiation time and irradiation amount of the sterilizing apparatus according to this embodiment, and FIG. 15 and FIG. 16 are graphs depicting inactivation levels of *Staphylococcus aureus* depending upon UV irradiation time and irradiation amount of the sterilizing apparatus according to this embodiment.

Next, operation and advantageous effects of the sterilizing apparatus according to this embodiment will be described with reference to FIG. 10 to FIG. 16.

Referring to FIG. 10 and FIG. 11, the sterilizing apparatus 200 according to this embodiment is disposed to open or close the drain hole 212 at the bottom of the wash basin 211 and sterilizes the drain basin 214 and the filter 215 inside the drain hole 212 in a closed state, and the sterilizing operation of the sterilizing apparatus 200 is controlled by the controller 150.

The operation of the sterilizing apparatus 200 for sterilizing the drain basin 214 and the filter 215 inside the drain hole 212 can be started by manipulating the switch 170 disposed on the handle 115.

For example, when the drain hole 212 is closed by the cover body 110 using the handle 115 and an operation signal is input through the switch 170, the signal is transmitted to the controller 150, which in turn starts to control the power supply 130 in response to the signal.

The detection unit 140 senses the location of the cover body 110 and obtains information about the location and posture of the cover body 110, and the controller 150 determines whether the drain hole 212 is open or closed by the cover body 110, based on the information about the location and posture of the cover body 110.

As a result, if it is determined that the drain hole 212 is closed by the cover body 110, the controller 150 controls the power supply 130 to supply power to the UV light emitting diode 120, and if it is determined that the drain hole 212 is open or is not properly closed by the cover body 110, the controller 150 controls the power supply 130 such that power is not supplied to the UV light emitting diode 120.

As such, the operation of the UV light emitting diode 120 is controlled only when the drain hole 212 is closed by the cover body 110, thereby preventing inefficient operation of the sterilizing apparatus 200, reducing accident risk, and preventing UV light emitted from the UV light emitting diode 120 from leaking to the outside of the cover body 110 and providing a harmful effect on the human body.

In this way, when power is supplied to the UV light emitting diode 120 through operation control of the controller 150, the UV light emitting diode 120 is turned on to emit ultraviolet light toward the drain basin 214 and the filter 215.

Here, the UV light emitting diode 120 emits UV light exhibiting strong sterilizing properties, for example, UV light having a peak wavelength in the range of 270 nm to 280 nm, more preferably UV light having a peak wavelength of 275 nm.

In this way, operation of the detection unit 140 is continued during operation of the UV light emitting diode 120, and during this operation, if it is determined that the drain hole 212 is open or is not properly closed by the cover body 110, based on the information about the location and posture of the cover body 110 obtained by the detection unit 140, the controller 150 controls the power supply 130 to stop power supply to the UV light emitting diode 120, whereby the UV light emitting diode 120 can be turned off to stop UV irradiation.

In addition, the UV light emitting diode 120 may be turned off when the power supply time of the power supply 130 set by the timer 180 has elapsed, and whether the UV light emitting diode 120 is turned on or off can be determined based on whether the visible light emitting diode 190 is turned on or off.

That is, in the sterilizing apparatus 200 according to this embodiment, UV irradiation can be performed only when the operation signal is input through the switch 170 in the state that the drain hole 212 is closed by the cover body 110; power supply can be automatically interrupted to stop UV irradiation when there is a risk of UV light leakage due to instability of the cover body 110 during operation of the cover body 110 or when a preset period of time has elapsed; and whether the UV light emitting diode 120 is turned on to emit UV light can be determined based on whether the visible light emitting diode 190 is turned on.

The sterilizing apparatus 200 according to this embodiment allows UV irradiation only when the safety conditions described above are satisfied, thereby further improving operation efficiency while effectively reducing accident risk and leakage of UV light.

On the other hand, UV light emitted from the UV light emitting diode 120 is directed to the drain basin 214 and the filter 215, thereby enabling sterilization of the drain basin 214 and the filter 215.

According to this embodiment, a plurality of UV light emitting diodes 120 is provided to the sterilizing apparatus such that the entire region of the drain basin 214 and the filter 215 can be irradiated with UV light, and the reflector 160 is disposed to reflect UV light emitted from the UV light emitting diodes 120 towards the drain basin 214 and the filter 215 so as to focus the UV light on the drain basin 214 and the filter 215, thereby enabling active sterilization over the entire region of the drain basin 214 and the filter 215.

In another example, with the filter 215 removed from the drain basin 214, UV light may be emitted towards the drain basin 214 to perform more active sterilization with respect to the drain basin 214 (see FIG. 12).

As sterilization effects through sterilization using the sterilizing apparatus 200 according to this embodiment described above, it can be seen that inactivation of E. coli approached 99.9% on the drain basin 214 and the filter 215 upon UV irradiation at a dose of about 5 mJ/cm$^2$ for about 15 minutes and most of E. coli remaining on the drain basin 214 and the filter 215 was sterilized during sterilization through UV irradiation (see FIG. 13 and FIG. 14).

In addition, it can be seen that inactivation of *Staphylococcus aureus* approached 99.9% on the drain basin 214 and the filter 215 upon UV irradiation at a dose of about 7 mJ/cm$^2$ for about 20 minutes and most of *Staphylococcus aureus* remaining on the drain basin 214 and the filter 215 was sterilized during sterilization through UV irradiation (see FIG. 15 and FIG. 16).

The sterilizing apparatus 200 according to this embodiment allows automatic UV sterilization with respect to the drain basin 214 and the filter 215 disposed inside the drain hole 212 through simple on/off operation, so that various bacteria remaining on the drain basin 214 and the filter 215 can be removed with high efficiency, thereby enabling easy, rapid and effective removal of bacteria present on the drain basin 214 and the filter 215 of the sink 210 at home.

In addition, the sterilizing apparatus 100 according to this embodiment allows UV irradiation only when various safety conditions, such as operation of the switch 170, detection of the closed state of the drain hole 212 through the detection unit 140, and operation time setting through the timer 180, are satisfied, thereby further improving operation efficiency of the sterilizing apparatus while effectively reducing accident risk and leakage of UV light.

Figure 17:
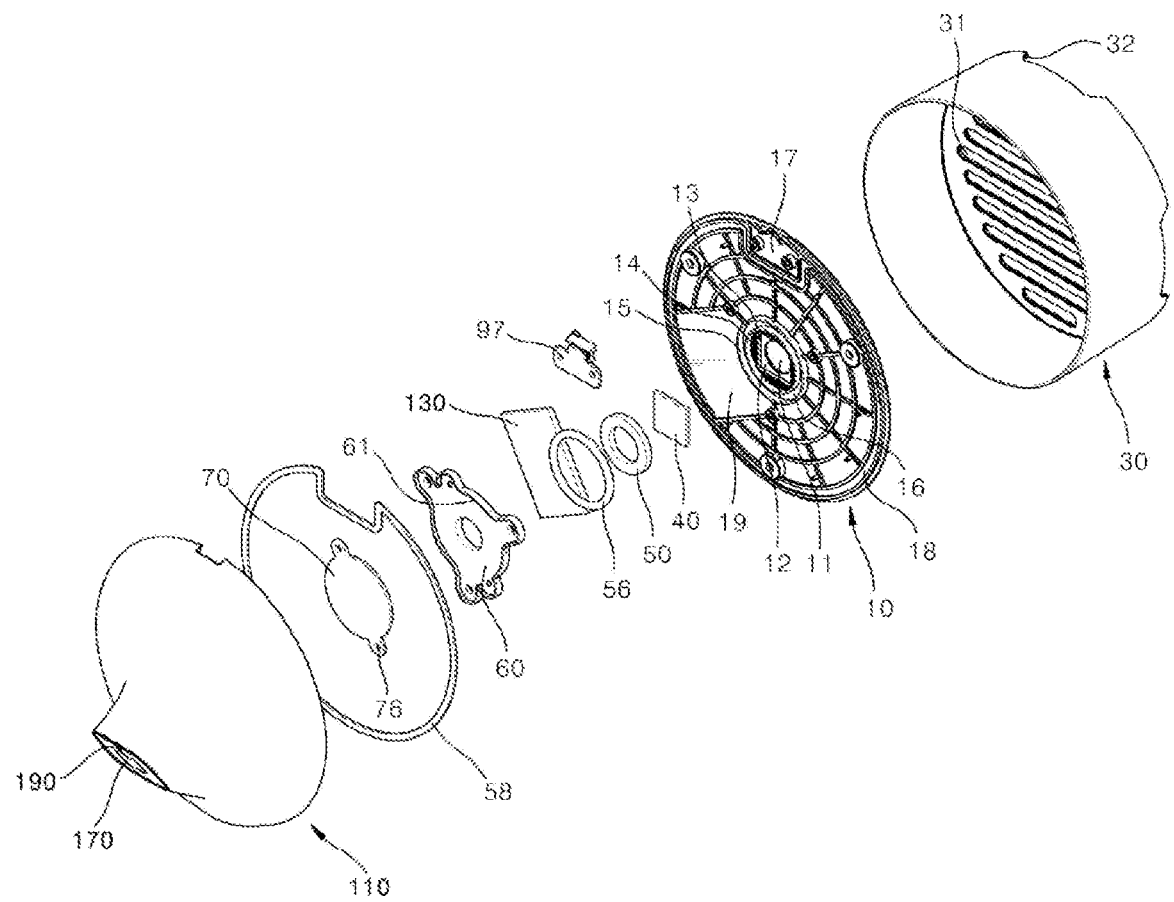
FIG. 17 is an exploded perspective view of a sterilizing apparatus according to another embodiment of the present invention.
Figure 18:
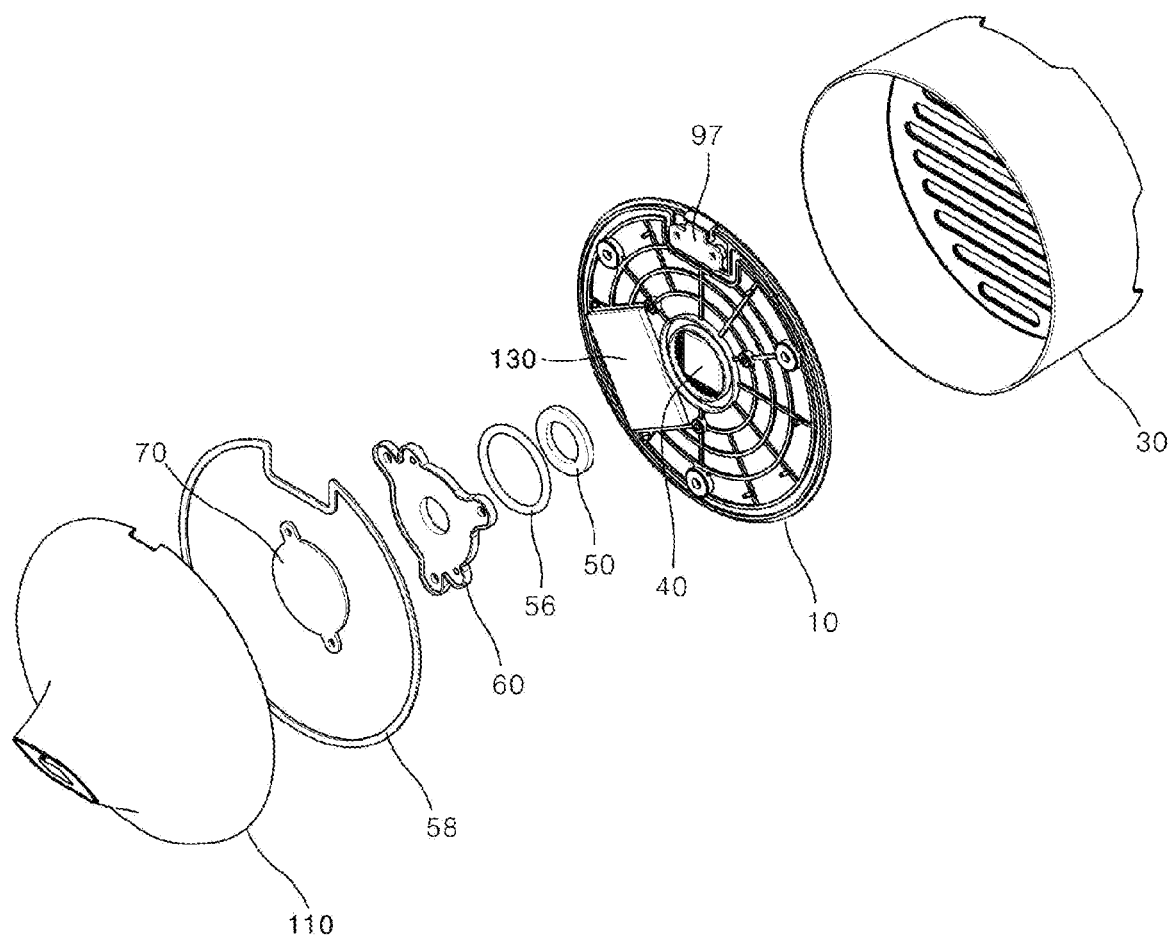
FIG. 18 is an exploded perspective view illustrating an assembled state of a window member, a battery and a charging terminal in FIG. 17.
Figure 19:
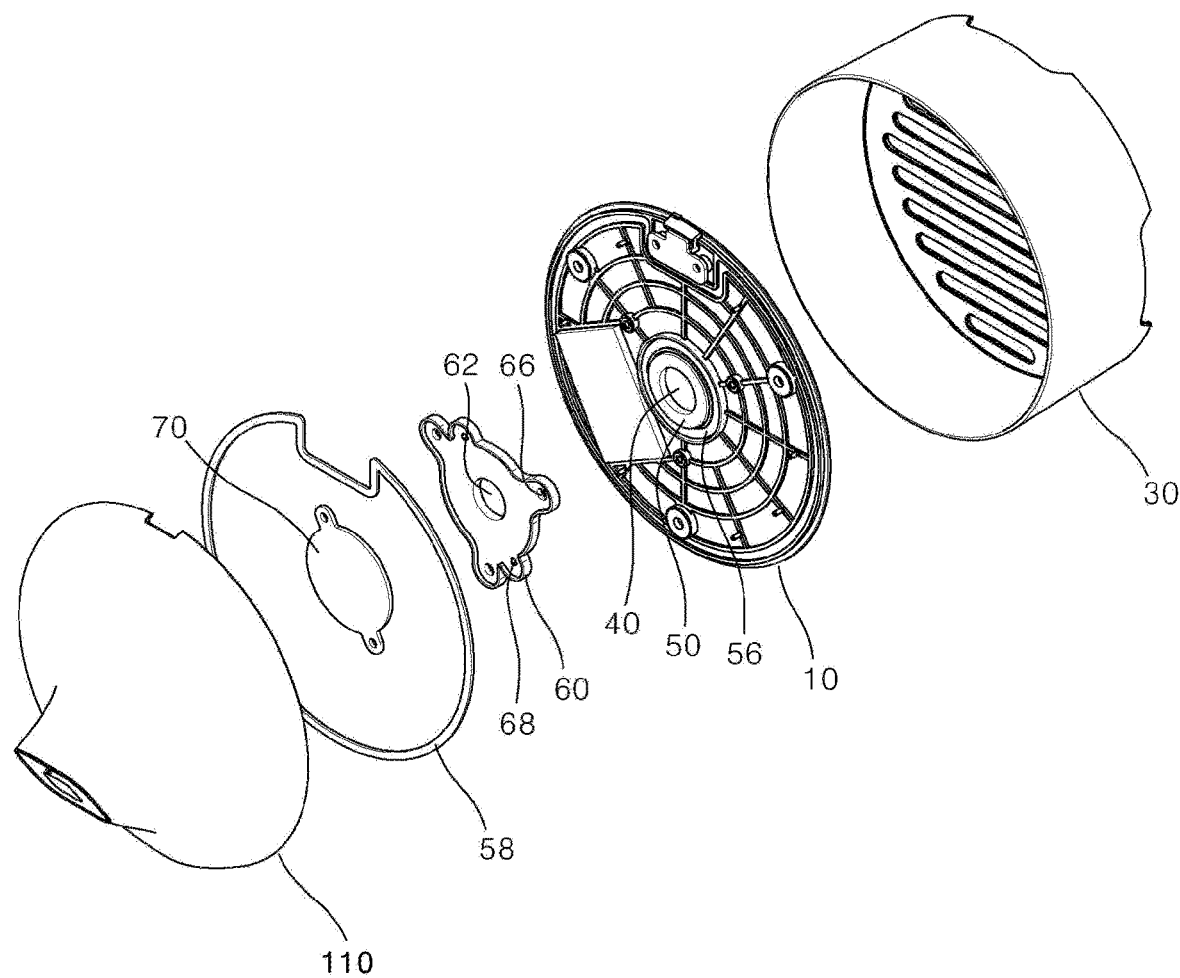
FIG. 19 is an exploded perspective view illustrating an assembled state of a first O-ring and a second O-ring in FIG. 18.
Figure 20:
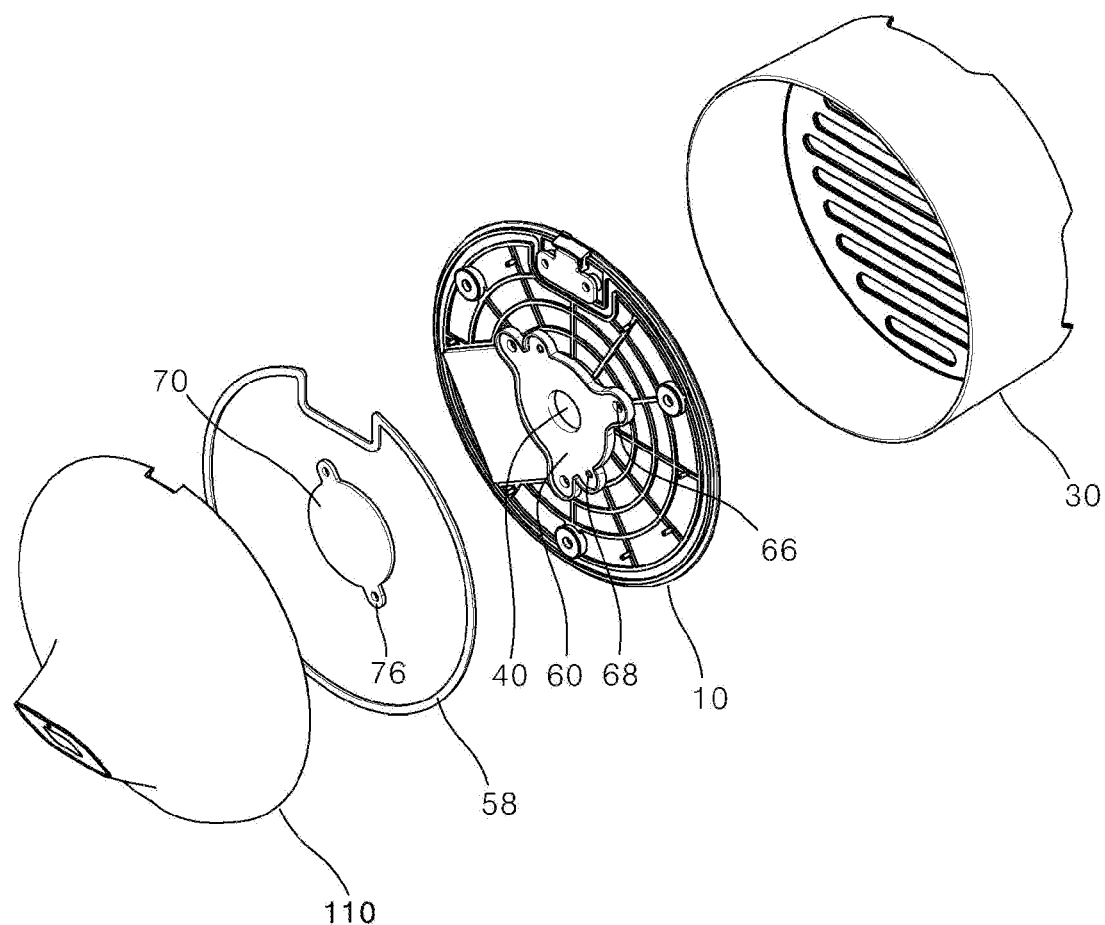
FIG. 20 is an exploded perspective view illustrating an assembled state of a compression member in FIG. 19.
Figure 21:
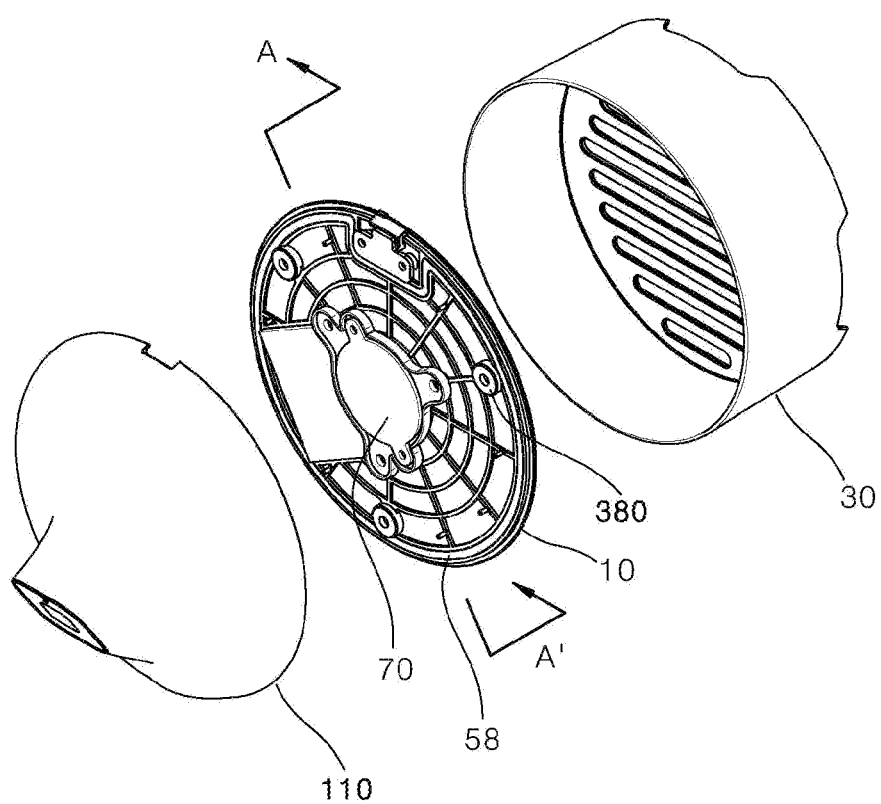
FIG. 21 is an exploded perspective view illustrating an assembled state of a substrate and a housing O-ring in FIG. 20.
Figure 22:
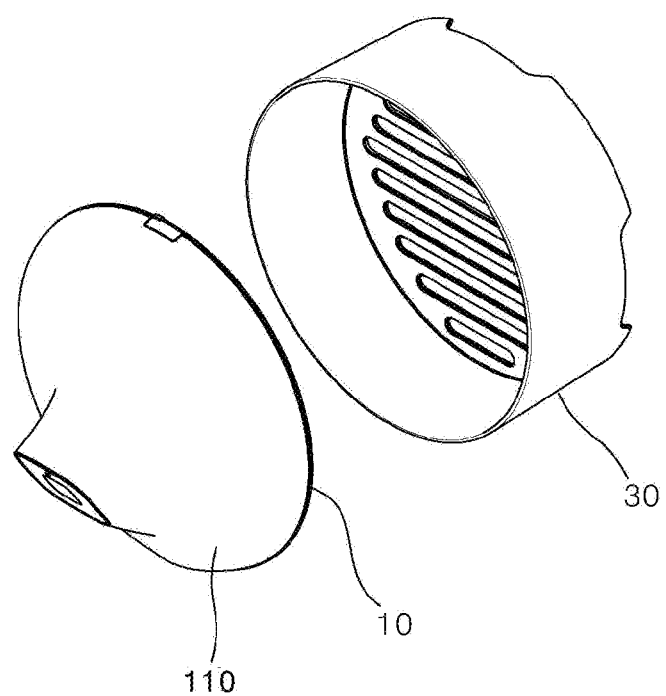
FIG. 22 is an exploded perspective view illustrating an assembled state of the sterilizer of FIG. 17, viewed from a different direction.
Figure 24:
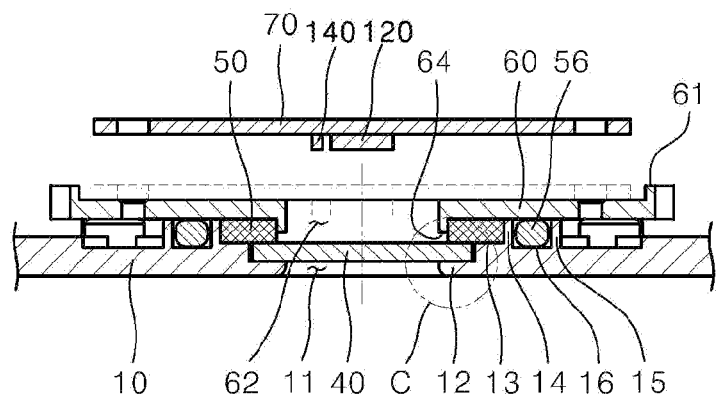
FIG. 24 is a cross-sectional view taken along line A-A' of FIG. 21.
Figure 25A:
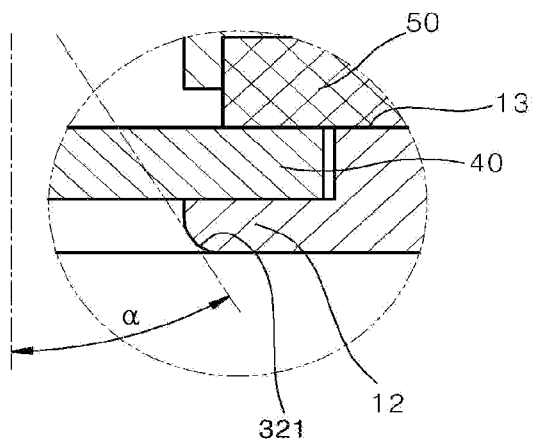
FIGS. 25A and 25B are enlarged views of Part C of FIG. 24.
Figure 25B:
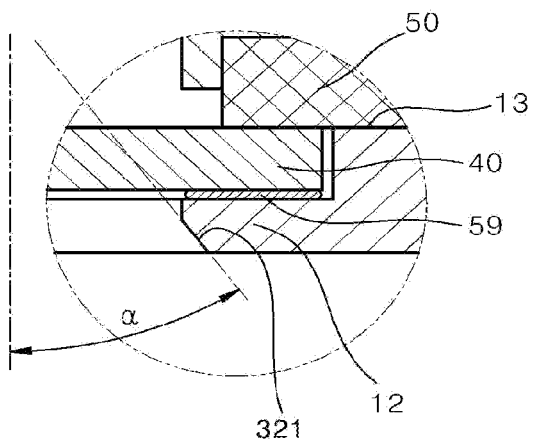
Figure 26:
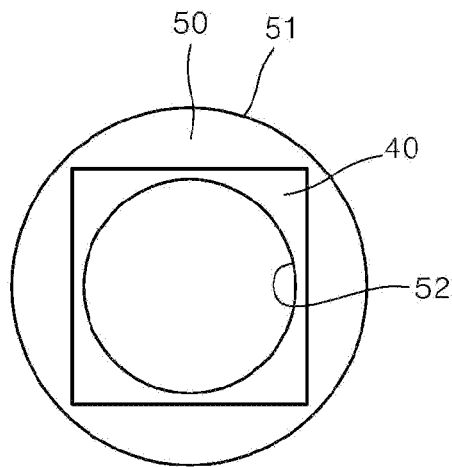
FIG. 26 is a plan view showing a state in which the window member is placed on the first O-ring.
Figure 27:
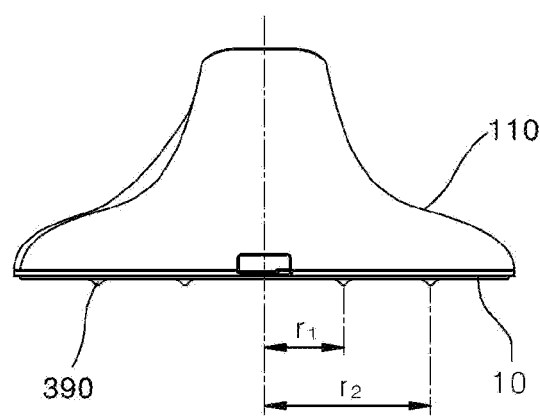
FIG. 27 is a front view showing a state in which the sterilizing apparatus according to the embodiment of the present invention is operable.

FIG. 17 is an exploded perspective view of a sterilizing apparatus according to another embodiment of the present invention, FIG. 18 is an exploded perspective view illustrating an assembled state of a window member, a battery and a charging terminal in FIG. 17, FIG. 19 is an exploded perspective view illustrating an assembled state of a first O-ring and a second O-ring in FIG. 18, FIG. 20 is an exploded perspective view illustrating an assembled state of a compression member in FIG. 19, FIG. 21 is an exploded perspective view illustrating an assembled state of a substrate and a housing O-ring in FIG. 20, FIG. 22 is an exploded perspective view illustrating an assembled state of the sterilizer of FIG. 17, viewed in a different direction, FIG. 24 is a cross-sectional view taken along line A-A' of FIG. 21, FIGS. 25A and 25B are enlarged views of Part C of FIG. 24, FIG. 26 is a plan view showing a state in which the window member is placed on the first O-ring, and FIG. 27 is a front view showing a state in which the sterilizing apparatus according to the embodiment of the present invention is operable.

Figure 23:
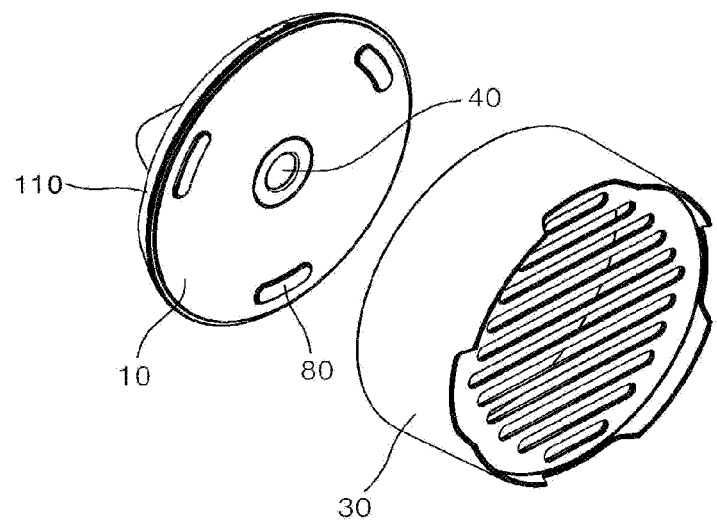
FIG. 23 shows an embodiment of a sterilizing apparatus.

Referring to FIG. 22 and FIG. 23, the sterilizing apparatus according to this embodiment includes a housing 10 which receives various components for sterilization; a cover body 110; and a holder 30 which holds the sterilizing apparatus. Four legs 32 of the holder 30 are placed on a flat floor, and the housing 10 and the cover body 110 are placed on the holder 30 to be secured thereto.

Referring to FIG. 17 and FIG. 27, in the sterilizing apparatus, the housing 10 is a flat portion and has a circular shape, and the cover body 110 has a curved shape and covers an upper portion of the housing 10. A bottom surface (see FIG. 27) is an outer surface of the housing 10 and faces a sterilizing target region. The housing 10 is provided at a central portion thereof with an irradiation opening 11, through which UV light emitted from a light source inside the cover body 110 is emitted. The cover body 110 is provided with a switch 170 for operating the sterilizing apparatus and a visible light emitting diode 190 for determining whether the sterilizing apparatus is operating.

First, a watertight structure and a window member protection structure disposed around the irradiation opening 11 of the housing 10 will be described. Referring to FIG. 17, FIG. 18 and FIG. 24, a square-shaped window member receiving portion 12 is formed on an inner surface of the housing 10 to enclose the irradiation opening 11 having a circular shape. A step portion 13 is formed around the window member receiving portion 12 to prevent a window member 40 fitted into the window member receiving portion 12 from moving to one side. The step portion 13 has substantially the same height as the window member 40 in a state that the window member 40 is received in the window member receiving portion 12. When the heights of the step portion and the window member are substantially the same, a step is not formed between upper surfaces of the window member 40 and the step portion 13, whereby sealing therebetween can be easily realized by placing a sealing member (first O-ring described below) between the window member and the step portion to be brought into close contact therewith.

The window member 40 may be quartz or fused silica, which is a material through which deep UV light emitted from a UV light emitting diode described below can be transmitted.

Referring to FIG. 18, FIG. 19 and FIG. 24, a first O-ring 50 is placed on the step portion 13 and the window member 40 fitted into the window member receiving portion 12 to cover at least a gap between the window member and the step portion. The first O-ring 50 has an annular shape, in which an outer circumferential surface 51 of the first O-ring 50 has a larger diameter than an outer circumference of the window member 40 and/or an inner circumference of the step portion and an inner circumferential surface 52 of the first O-ring has a smaller diameter than the window member 40 (see FIG. 26). Thus, when the first O-ring 50 is placed on the step portion 13 and the window member 40 fitted into the window member receiving portion 12, the gap between the window member and the step portion is shielded by the first O-ring 50.

As shown in the drawings, a first jaw 14 is formed outside a region in which the first O-ring 50 is placed, and regulates the location of the first O-ring 50. In addition, a second O-ring receiving groove 16 into which a second O-ring 56 is fitted is formed outside the first jaw 14 and a second jaw 15 having substantially the same height as the first jaw 14 is formed outside the second O-ring receiving groove 16. The second O-ring receiving groove 16 receives the second O-ring described later. In this way, according to this embodiment, the sterilizing apparatus has a double-sealing structure in a path where water penetration is likely to occur, thereby securing waterproof characteristics. In particular, when the two jaws 14, 15 have the same height, the second O-ring can be more easily received and can be uniformly expanded without uneven distribution of compressive force when the second O-ring is pressed by a compression member described below.

Referring to FIG. 19, FIG. 20 and FIG. 24, the compression member 60 is formed in a shape of an annular flat plate, and includes a circular hole 62 formed at the center thereof, a rib 61 formed at an outer circumference thereof to reinforce the compression member 60, and three fastening portions 66 formed at the outer circumference thereof and arranged at intervals of 120 degrees. A fastening screw (not shown) penetrates each of the fastening portions 66 and is screwed to an inner surface of the housing such that the compression member 60 is strongly pressed and secured to the inner surface of the housing 10.

Such a compressive force is transmitted to the first O-ring 50 and the second O-ring 56 such that an upper surface of the first O-ring is brought into close contact with the compression member 60 and a lower surface of the first O-ring is brought into close contact with the upper surfaces of the window member 40 and the step portion 13. When the first O-ring 50 is pressed, the first O-ring 50 is pushed by the pressure such that the outer circumferential surface 51 of the first O-ring 50 expands in a direction of increasing the diameter thereof and the inner circumferential surface 52 thereof expands in a direction of decreasing the diameter thereof. The outer circumferential surface 51 of the first O-ring is prevented from expanding by the first jaw 14 and brought into close contact with the first jaw 14. On the other hand, the inner circumferential surface of the first O-ring is prevented from expanding by a protruding jaw 64 protruding in the direction of the window member, that is, downward, around the hole 62 of the compression member 60. At this time, a lower end of the protruding jaw 64 does not contact the window member 40 and is separated a certain distance from the window member to have a gap therebetween. Since the window member 40 can be damaged due to intensive pressure from the protruding jaw 64 when the protruding jaw 64 is brought into contact with the window member 40, a predetermined gap is required between the window member and the protruding jaw. On the other hand, since the inner circumferential surface of the first O-ring can freely expand inwards in a structure wherein the compression member 60 does not include the protruding jaw 64, adherence between the inner circumferential surface of the first O-ring, the compression member and the window member can be deteriorated. Accordingly, the protruding jaw 64 may be formed to have a sufficient height to be uniformly pressed between the window member and the first O-ring without applying intensive pressure to the window member in consideration of the material of the first O-ring and the like. In other words, as the height of the protruding jaw is lowered, the possibility of applying the intensive pressure to the window member becomes higher, whereas uniformity of the pressure applied between the window member and the first O-ring is lowered. As the height of the protruding jaw is increased, the possibility of applying the intensive pressure to the window member increases, whereas it is more advantageous to secure uniformity of the pressure applied between the window member and the first O-ring. An optimal height of the protruding jaw may be determined so as to satisfy the above conditions in consideration of the material of the first O-ring and the gap between the protruding jaw and the window member.

A cross-sectional area of the second O-ring 56 is set to be slightly larger than a cross-sectional area defined by the second O-ring receiving groove 16, the first jaw 14, the second jaw 15 and the compression member. Thus, when the second O-ring is pressed by the compression member, an outer surface of the second O-ring is brought into contact with the second O-ring receiving groove 16, the first jaw 14, the second jaw 15 and the compression member under uniform pressure.

Among materials theoretically having a hardness of 0 to 100, the first O-ring 50 is formed of a ductile silicone material having a hardness of less than 30. If the hardness is greater than 30, there is a high possibility that the intensive pressure is applied to a certain portion of the window member 40 to be damaged when the first O-ring is pressed by the compression member. It should be understood that the compression member may be formed of a material having a higher hardness than the first O-ring, such as ABS resins.

As shown in FIG. 25B, the compression member may further include an additional elastic material 59 interposed between the window member 40 and the window member receiving portion 12. The elastic material 59 has an effect of eliminating a possibility of pressure concentration at a specific portion between the window member and the window member receiving portion while improving a watertight effect through adherence of the elastic member.

On the other hand, the hole 62 of the compression member 60 is concentrically aligned with the irradiation opening 11 of the housing 10. Both the hole 62 of the compression member and the irradiation opening 11 of the housing 10 have a circular shape. The inner circumferential surface of the first O-ring also coincides with the center of these holes and has a circular shape. This structure is provided in consideration of an irradiation pattern of the light emitting diode which emits light in the form of diffusing the light in a conical shape from a spot light source, and can cause the compressive force between the compression member 60 and the housing 10 to be uniformly distributed between the first O-ring 50 and the window member 40 and can minimize an exposed area of the window member while securing as large a UV irradiation area as possible.

Alternatively, the window member 40 may have a square shape. With this structure, the window member can be easily manufactured and prevented from laterally moving or rotating in place when the location of the window member is restricted by the step portion 13. The shapes of the window member 40 and the first O-ring 50 have been described above with reference to FIG. 26.

Next, referring to FIG. 20, FIG. 21, FIG. 24 and FIGS. 25A and 25B, a substrate 70 is secured to an upper surface of the compression member 60. The substrate 70 is provided with fixing portions 76 at two locations opposite to each other with respect to the center of the substrate and a fastening screw is screwed to a fixing portion 68 of the compression member 60 through each of the fixing portions 76. The locations of the fixing portions 68 may be determined so as not to overlap the locations of the fastening portions 66 of the compression member described above.

On the substrate 70, the UV light emitting diode 120 is mounted at a location concentrically aligned with the irradiation opening 11 and the hole 62 while facing the irradiation opening 11 and the hole 62. By way of example, the UV light emitting diode 120 may have an irradiation angle of 120 degrees. UV light emitted from the UV light emitting diode 120 is emitted to the outside after passing through the window member 40 and the irradiation opening 11. As a result, a sterilization region facing the housing 10 is exposed to UV light. For example, the irradiation opening 11 may have a smaller diameter, such that at least 50% of the amount of UV light emitted from the UV light emitting diode 120 can pass therethrough.

In order to secure the irradiation angle of the UV light emitting diode as much as possible, the irradiation opening 11 may include an irradiation opening-enlarged portion 321, which has a cross section gradually widened toward the outside (see FIGS. 25A and 25B). The irradiation opening-enlarged portion 321 may have a curved shape as shown in FIG. 25A or may have a tapered shape as shown in FIG. 25B. With any shape, the irradiation opening-enlarged portion 11 secures an irradiation area (a) corresponding as much as possible to the irradiation angle of UV light emitted from the UV light emitting diode, while securing an area for supporting the window member 40 as much as possible. For example, in a structure wherein the irradiation opening 11 does not include the irradiation opening-enlarged portion 11, the diameter of the irradiation opening 11 must be increased so as to increase the irradiation area by a, thereby causing reduction in the area of the window member receiving portion that supports the window member. In addition, since the diameter of the hole 62 of the compression member 60 must be increased corresponding to increase in the diameter of the irradiation opening 11 (when the hole of the compression member has a smaller diameter than the irradiation opening, pressure is unevenly applied to the upper and lower surfaces of the window member, thereby increasing a possibility of damage to the window member), the unsupported area of the upper and lower surfaces of the window member 40 is increased, thereby increasing the possibility of damage to the window member 40. However, according to this embodiment, the irradiation opening 11 is formed with the irradiation opening-enlarged portion 11, thereby reducing the possibility of damage to the window member 40 while securing the irradiation region of UV light as much as possible.

By way of example, the UV light emitting diode 120 emits deep UV light having a peak wavelength of 275 nm.

The UV light source used in the present invention is the UV light emitting diode 120, which has high directionality in one direction. The UV light emitting diode allows fine adjustment of the peak wavelength of light emitted therefrom depending upon the proportion of components thereof. Therefore, efficiency of UV light can be increased through use of a UV light emitting diode configured to emit light having a peak wavelength most efficient for UV sterilization.

Generally, UV having a peak wavelength of 253 nm is known to have the highest sterilizing power. However, as a result of actual experiments, it was confirmed that the most germicidal wavelength was 270 nm in sterilization of bacteria contained in water.

Figure 28:
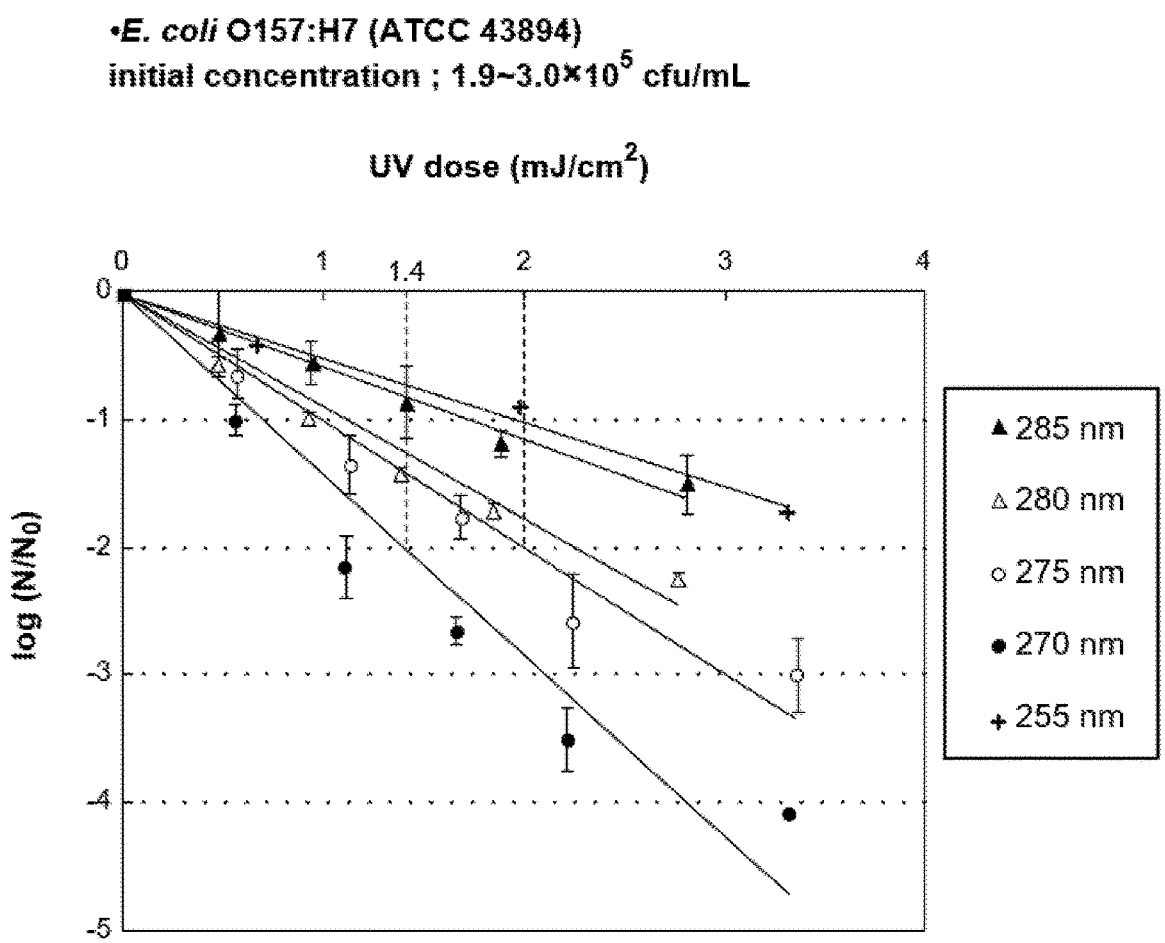
FIG. 28 is a graph showing a relationship between UV irradiation dose and sterilization rate after mixing E. coli O157:H7 (ATCC 43894) with water and irradiating the mixture with UV light at different wavelengths.

FIG. 28 is a graph showing a relationship between UV irradiation dose and sterilization rate after mixing *E. coli* O157:H7 (ATCC 43894) with water and irradiating the mixture with UV light at different wavelengths. An initial concentration of bacteria contained in water was 1.9 to $3.0 \times 10^5$ cfu/mL. Experiments were performed under the same conditions excluding the wavelength of UV light.

Experimental results showed a sterilization rate of 99% upon irradiation with UV light having a wavelength of 270 nm at a dose of 1.4 mJ/cm$^2$, which was much superior to UV light of other wavelengths.

Figure 29:
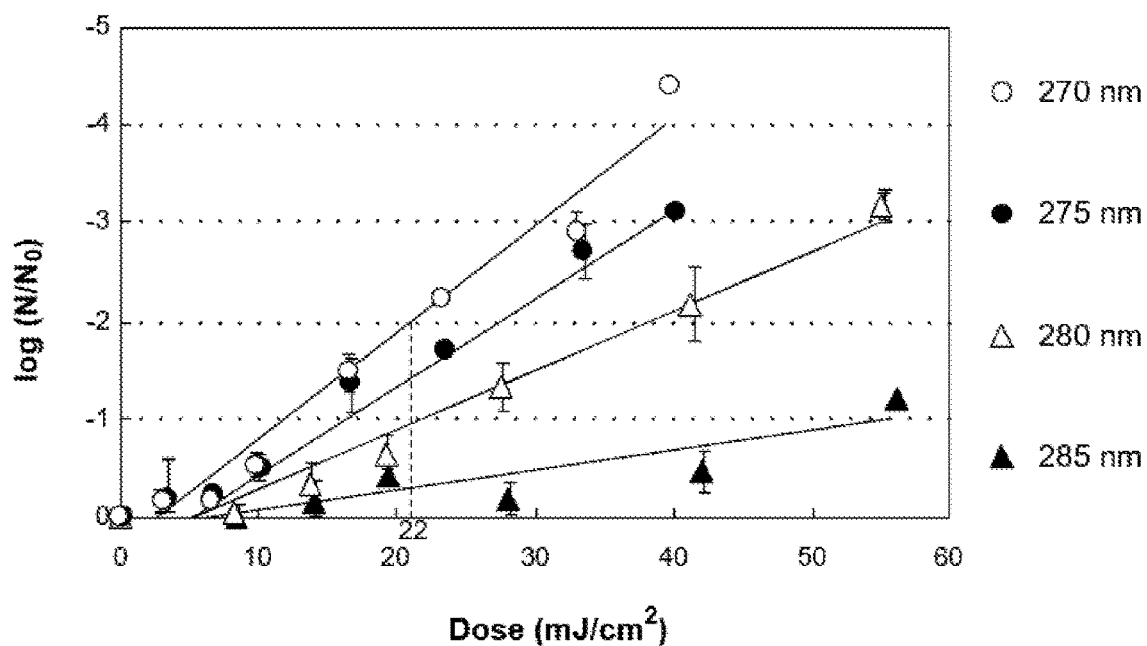
FIG. 29 is a graph showing a relationship between UV irradiation dose and sterilization rate after mixing B. subtilis spores (ATCC 6633) with water and irradiating the mixture with UV light at different wavelengths.

FIG. 29 is a graph showing a relationship between UV irradiation dose and sterilization rate after mixing *B. subtilis* spores (ATCC 6633) with water and irradiating the mixture with UV light at different wavelengths.

Experimental results showed a sterilization rate of 99% upon irradiation with UV light having a wavelength of 270 nm at a dose of 22 mJ/cm$^2$, which was much superior to UV light of other wavelengths.

Figure 30:
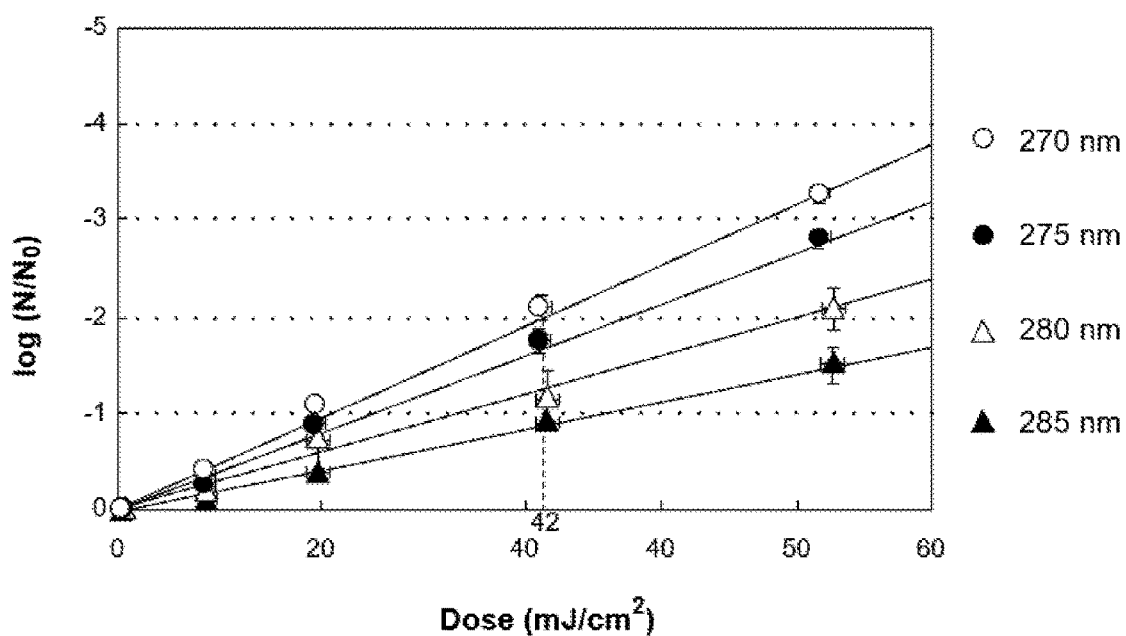
FIG. 30 is a graph showing a relationship between UV irradiation dose and sterilization rate after mixing B. MS2 phage (ATCC 15597-B1) with water and irradiating the mixture with UV light at different wavelengths.

FIG. 30 is a graph showing a relationship between UV irradiation dose and sterilization rate after mixing B. MS2 phage (ATCC 15597-B1) with water and irradiating the mixture with UV light at different wavelengths.

Experimental results showed a sterilization rate of 99% upon irradiation with UV light having a wavelength of 270 nm at a dose of 42 mJ/cm$^2$, which was much superior to UV light of other wavelengths.

As a result of analysis of the experimental results, it was concluded that DNA or RNA of bacteria or viruses contained in water could be more sensitive to UV light having a wavelength of 270 nm. Since most of bacteria and viruses entering the body through food consumed by a person depend on moisture of the food and a sink drain also has an environment rich in food waste and water, it can be concluded that the above experiments were performed under conditions sufficiently reflecting an actual region to be sterilized.

Consequently, it was confirmed that sterilization efficiency was decreased with increasing or decreasing wavelength from 270 nm. Accordingly, in the present invention, the UV light emitting diode configured to emit UV light having a peak wavelength within the range of about 10 nm from 270 nm is used to improve sterilization efficiency with respect to bacteria or microorganisms.

Although the sterilizing apparatus according to the embodiments employs the UV light emitting diode 120 configured to emit UV light having a peak wavelength in a wavelength band slightly deviating from a wavelength of 253 nm, which is the best absorption wavelength for human DNA, UV light emitted from the UV light emitting diode 120 is still detrimental to humans. Therefore, there is a need for a safety device for allowing UV irradiation of the sterilizing apparatus only in the case of sterilization.

As shown in FIG. 24, the sterilizing apparatus according to the present invention is provided with a plurality of detection units detecting different factors. Since the sterilizing apparatus according to the embodiments can employ deep UV light, the sterilizing apparatus requires a safety device which allows operation of the sterilizing apparatus for UV irradiation only when all environments measured by the plurality of detection units satisfy all conditions for use of the sterilizing apparatus.

For example, since the sterilizing apparatus according to the embodiments acts as a lid for covering the drain hole of the sink to block external light (visible light), it can be defined that a region where sterilization is performed is in a dark state. In addition, upon sterilization, the drain hole of the sink is placed to allow the outer surface of the housing to face in the direction of gravity. Further, upon sterilization of the drain hole, a front side of the sterilizing apparatus is not separated a distance of 20 cm or more (depth of the drain hole) from the outer surface of the housing.

For measurement under such an environment, in the sterilizing apparatus according to the present invention, the detection unit 140 may be placed near the UV light emitting diode 120 mounted on the substrate 70. The detection unit 140 includes an illuminance sensor for detecting visible light entering the housing through the irradiation opening 11. The illuminance sensor is provided to check whether the environment for use of the sterilizing apparatus is a dark environment.

However, this structure alone has limitations in guaranteeing a suitable environment for use of the sterilizing apparatus. For example, if the dark environment is obtained by turning off all lights in a room, the illumination sensor alone cannot guarantee the suitable environment for use of the sterilizing apparatus.

Therefore, in the sterilizing apparatus according to the present invention, the detection unit 140 disposed on the substrate 70 may further include a distance sensor (for example, an IR sensor). The distance sensor of the detection unit measures a distance of an object in front of the outer surface of the housing through the irradiation opening 11. If the measured distance is greater than a reference distance (the distance that the object is placed in front of the housing upon normal sterilization), it can be determined that the sterilizing apparatus is not in an environment suitable for use.

In addition, the sterilizing apparatus according to the present invention may further include a posture sensor (for example, a gyro sensor or a tilt sensor). Since the sterilizing apparatus according to the present invention is used in the form of a lid, the housing of the sterilizing apparatus faces the floor under normal use conditions (see FIG. 27) Therefore, if it is detected that the sterilizing apparatus does not face the floor, it can be determined that the sterilizing apparatus is not in the environment suitable for use.

According to the present invention, the substrate 70 may have a control circuit that enables power supply to the UV light emitting diode only when all of conditions measured by the plurality of sensors for measuring such various environments satisfy safety standards.

It should be noted that operation of turning on or off the UV light emitting diode 120 is primarily controlled by the switch 170 and, even when the switch 170 is switched on, power supply to the UV light emitting diode 120 is interrupted in the case where all of the conditions measured by the plurality of sensors do not satisfy the safety standards.

The sterilizing apparatus according to the present invention further includes a visible light emitting diode 190 which is disposed near the switch 170 and is connected in series to the UV light emitting diode to be turned on or off together with the UV light emitting diode. The visible light emitting diode may be used to confirm, by the naked eye, whether the UV light emitting diode is turned on. In this way, when the visible light emitting diode is connected in series to the UV light emitting diode, the visible light emitting diode 190 and the UV light emitting diode 120 are turned on or off at the same time. Accordingly, a user can conveniently determine whether the sterilizing apparatus is operated by checking with the naked eye whether the visible light emitting diode is turned on or off. In the structure wherein the visible light emitting diode is connected in series to the UV light emitting diode, if either the UV light emitting diode or the visible light emitting diode fails, both the UV light emitting diode and the visible light emitting diode do not operate when the visible light emitting diode is not turned on due to failure of the visible light emitting diode. Therefore, it can be ensured that the UV light emitting diode also does not operate if the visible light emitting diode is not turned on.

Sterilization may be performed by UV light or by removing moisture to create a dry environment. In the present invention, a far infrared light source may be further disposed on the substrate 70 to realize both UV irradiation and a drying function. The far infrared light source can further increase the sterilizing effect by drying a sterilization region by emitting far infrared rays to the sterilization region through the irradiation opening 11.

Referring to FIG. 20 to FIG. 23, a housing O-ring 58 is press-fitted into a housing O-ring receiving groove 18 formed along a contact portion between the housing 10 and the cover body 110 facing each other when the housing 10 and the cover body 110 are fastened to each other. As described above, water tightness can be secured not only around the irradiation opening 11 but also at the contact portion between the housing 10 and the cover body 110, thereby ensuring waterproofing of the interior space in the housing 10 and the cover body 110 fastened to each other. The sterilizing apparatus according to the present invention requires a sufficient degree of waterproofing to prevent water from entering the sterilizing apparatus, for example, when tap water is accidentally supplied to the sink.

In order to fasten the housing 10 to the cover body 110, a fastening screw (not shown) is fitted from the outer surface of the housing 10 into the cover body 110, as shown in the drawings. Then, the fastening screw is screwed to the cover body through a fastening hole 380 of the housing. In addition, a support member 80 is provided to the outer surface of the housing 10 on which the fastening hole 380 is formed. The support member 80 is formed of, for example, a rubber-like elastic material that can achieve both a slipping prevention effect and a sealing effect, thereby prevent water from penetrating through the fastening hole 380 and allowing the sterilizing apparatus to be maintained in place without slipping on a surface on which the sterilizing apparatus is placed.

In the present invention, a power source for operating the UV light emitting diode may be supplied from the power supply 130 embedded in the sterilizing apparatus. For example, the power supply 130 is a secondary battery. The power supply 130, the substrate 70, and the switch 170 are electrically connected to one another inside the cover body 110 and the housing 10. In addition, the power supply 130 is electrically connected to a charging terminal 97. Here, the charging terminal 97 is a path through which power is supplied from an external power source to charge the power supply 130. An inlet of the charging terminal 97 is exposed to the outside of the cover body 110 and the housing 10 and a watertight cap is detachably fitted to the inlet of the charging terminal 97. Thus, during charge of the power supply 130, the charging terminal 97 may be connected to an external power source after removing the watertight cap from the inlet thereof. According to this embodiment of the present invention, the sterilizing apparatus has the structure wherein the charging terminal is secured outside the housing O-ring 58 in order to secure additional water tightness with respect to the interior region between the cover body 110 and the housing 10 and a portion to be protected from water on the charging terminal is covered by silicone, as shown in the drawings. With this structure, when water permeates towards the charging terminal not covered by the watertight cap, the water is prevented from entering the interior region between the cover body 110 and the housing 10. Thus, there is no need to dry other components except the charging terminal.

The sterilizing apparatus according to the present invention may be used in sterilization of various objects. For example, even the drain hole of the sink may have different specifications (diameters). In consideration of this point, the sterilizing apparatus according to the present invention includes an alignment protrusion 390 formed on the outer surface of the housing 10, as shown in FIG. 27. The sterilizing apparatus may include a plurality of alignment protrusions 390 concentrically arranged on the outer surface of the housing 10 at locations of different diameters r1, r2 with respect to the irradiation opening. The alignment protrusions may be provided in the form of an annular ring centered on the UV irradiation opening, a part of the annular ring, or a set of points located on the annular ring. These diameters r1 and r2 can be determined corresponding to the diameter of a drain hole of available sinks.

The sterilizing apparatus according to the present invention may also be used to sterilize the interior of each of various containers after being placed on a lid of the corresponding container. For example, sterilization may be performed after placing the sterilizing apparatus at an entrance of a cup or tumbler that is too deep for the hand of a user to reach into.

The sterilizing apparatus according to the present invention may further include a holder 30, as shown in the drawings. The holder has a hollow cylindrical shape having a low height and blocked at a side surface thereof, and includes a vent hole 31 formed in a bottom surface and a plurality of legs 32 extending below the bottom surface to allow smooth communication with external air through the vent hole.

In order to dry and sterilize a scrubber after dish washing, the scrubber may be sterilized using the sterilizing apparatus after placing the sterilizing apparatus on the holder 30, with the scrubber placed inside the holder 30. In addition, not only kitchen utensils such as scrubbers but also objects having a size to be received in the holder can be sterilized using the sterilizing apparatus.

Figure 31:
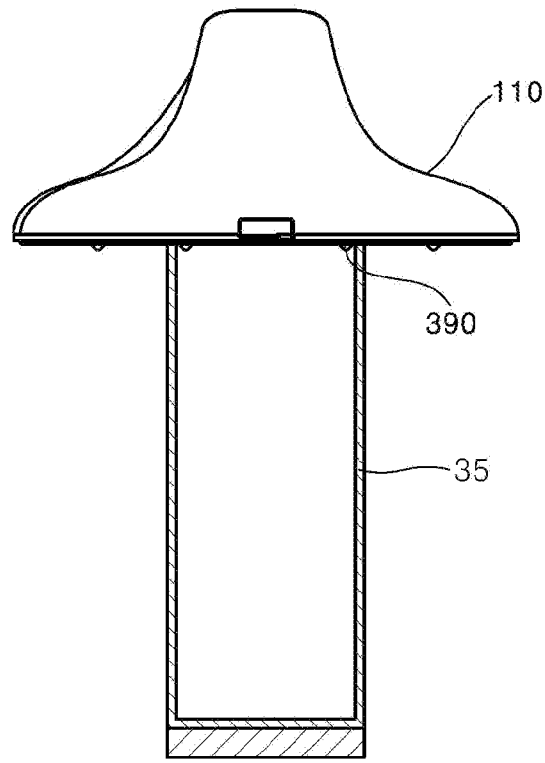
FIG. 31 and FIG. 32 are views illustrating other examples of use of the sterilizing apparatus according to the embodiment of the present invention.
Figure 32:
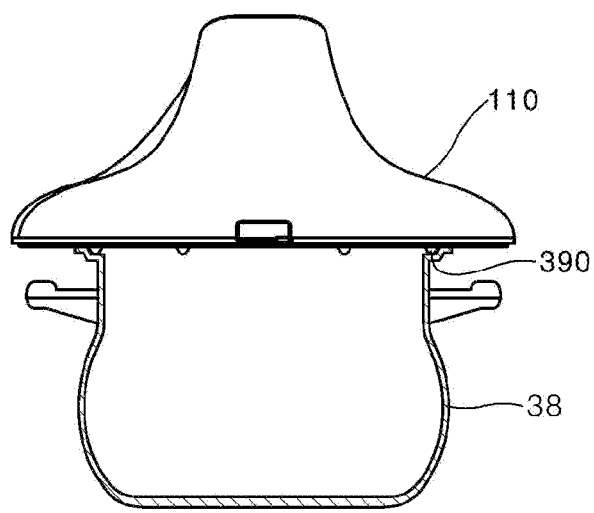

The sterilizing apparatus according to the present invention may also be used for sterilization not only of the drain hole of the sink but also various other objects. For example, in sterilization of a tumbler 35 or a pot 38 which requires internal sterilization, the tumbler 35 or the pot 38 is covered by the sterilizing apparatus instead of a lid, as shown in FIG. 31 and FIG. 32.

Next, operation of the sterilizing apparatus according to the present invention will be described.

A user places the sterilizing apparatus on the holder 30 or puts it on the floor and charges the power supply 130 by connecting an external power source thereto through the charging terminal 97. The degree of charge is indicated by a color of the visible light emitting diode 190. After charging the power supply, the sterilizing apparatus with the watertight cap fitted into the charging terminal 97 is placed on a drain hole of a sink. At this time, the center of the sterilizing apparatus can be efficiently aligned with the center of the drain hole by the alignment protrusions 390 protruding toward the floor, and the sterilizing apparatus is fixed in place by the support member 80 without slipping.

Figure 33:
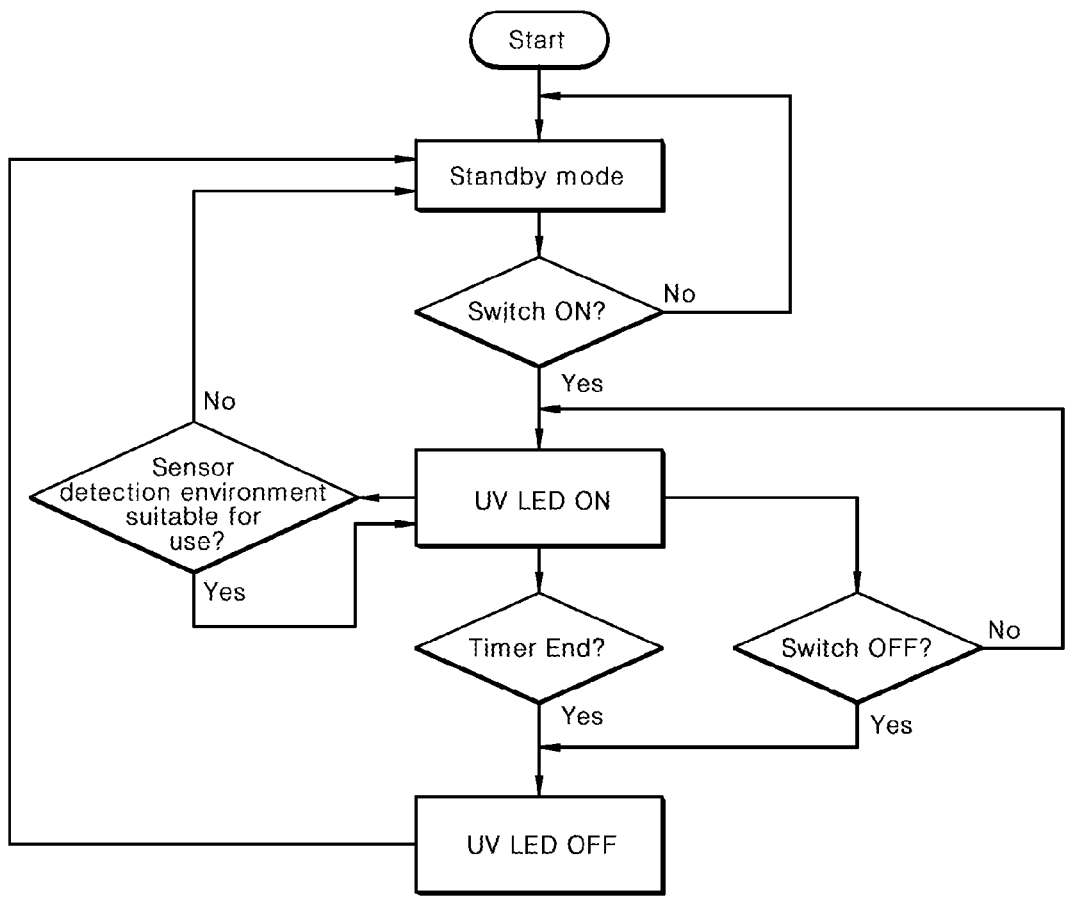
FIG. 33 is a flowchart illustrating operation of the sterilizing apparatus according to the embodiment of the present invention.

FIG. 33 is a flowchart illustrating operation of the sterilizing apparatus according to the embodiment of the present invention.

When a user presses the switch 170, the control circuit on the substrate 70 checks environmental measurement results of various sensors. That is, under conditions wherein illuminance of visible light measured by the illuminance sensor is lower than a reference value, an object is detected within a predetermined distance from the irradiation opening by the distance sensor, and the sterilizing apparatus emits UV light in the downward direction (that is, the sterilizing apparatus is horizontally well placed), power is supplied to the UV light emitting diode 120 by the control circuit. When there is no abnormal operation of both the UV light emitting diode 120 and the visible light emitting diode 190, the visible light emitting diode 190 is also turned on together with the UV light emitting diode 120, whereby a user can confirm whether the sterilizing apparatus is operating.

The sterilizing apparatus operates as a timer. For example, after power is supplied to the UV light emitting diode for a sufficient period of time for sterilization, the power source is interrupted again to turn off the sterilizing apparatus. Experimental results showed that the sterilizing apparatus according to the embodiment of the present invention secured 259.9% of sterilization even when the sterilizing apparatus was operated for about 30 to 40 minutes. When a time set by the timer has elapsed, the visible light emitting diode 190 blinks. The visible light emitting diode may be turned off after blinking several times, or may continue to blink until a user confirms that the time set by the timer has elapsed.

If the sterilizing apparatus is inadvertently struck or raised before the time set by the timer elapses, at least one of the sensors detects that the use environment is out of safety conditions and power supply is immediately shut off. Of course, even in the case where the time set by the timer time has not elapsed, the power supplied to the UV light emitting diode is immediately shut off when a user switches off the sterilizing apparatus.

In this way, the sterilizing apparatus can improve quality of life through sterilization around the drain hole of the sink by inhibiting reproduction of bacteria or fungi while removing odors. In addition, sterilization of other products can also be performed using the holder and the like by the method as described above.

Although some exemplary embodiments have been described herein, it should be understood by those skilled in the art that these embodiments are given by way of illustration only, and that various modifications, variations, and alterations can be made without departing from the spirit and scope of the present invention. In addition, although advantageous effects provided by a certain configuration are not clearly described in description of the exemplary embodiments, it should be noted that expectable effects of the corresponding configuration should be acknowledged.

What is claimed is:
1. A sterilizing device, comprising;
a housing having an outer surface facing a target region and an inner surface opposite to the outer surface;
a cover body coupled to the housing defining a space inside the housing and cover an upper portion of the housing;
an irradiation opening disposed on the housing facing the target region;
a light source disposed on a substrate in the housing and configured to emit light toward the target region through the irradiation opening;
a power supply configured to supply power to the light source;
a controller configured to control a power supply time of the power supply according to a preset period of time; and
a charging terminal electrically connected to the power supply and providing a path through which power is supplied from an external power source to charge the power supply,
wherein the light source includes light emitting elements and the light emitting elements are disposed on the substrate to be spaced apart from one another by a predetermined interval such that a surface of a target in the target region is evenly irradiated with the light emitted by the light emitting elements, wherein the irradiation opening has a diameter allowing at least 50% of the light emitted from the light source to pass therethrough.

2. The sterilizing device of claim 1, wherein the light emitting elements comprise:
a first light emitting element; and
a second light emitting element,
wherein the first light emitting element and the second light emitting element have different peak wavelengths from each other.

3. The sterilizing device of claim 2, wherein the first light emitting element has a peak wavelength to inactivate at least one pathogen included in the target region.

4. The sterilizing device of claim 2, wherein the second light emitting element has a peak wavelength in a visible range and disposed near the first light emitting element.

5. The sterilizing device of claim 2, wherein the second light emitting element is configured to be turned on simultaneously with the first light emitting element such that the first light emitting element and the second light emitting element operate together.

6. The sterilizing device of claim 1, wherein the light source further comprises a light transmissive member including a material through which deep UV light emitted from the light source is transmitted.

7. The sterilizing device of claim 1, wherein the irradiation opening has an irradiation opening-enlarged portion having a cross-section gradually widening along a direction away from the light source.

8. The sterilizing device of claim 1, further comprising;
a reflector disposed on the cover body and including a material having a reflectivity to reflect the light emitted from the light source.

9. The sterilizing device of claim 1, wherein the light source is configured to emit the light at a dose between 5 mJ/cm$^2$ and 20 mJ/cm$^2$ to inactivate a pathogen including *E. coli* that is included in the target within the target region.

10. The sterilizing device of claim 1, wherein the light source is configured to emit the light at a dose between 7 mJ/cm$^2$ and 20 mJ/cm$^2$ to inactivate a pathogen including *Staphylococcus aureus* that is included in the target within the target region.

11. A sterilizing device, comprising;
a housing having an outer surface facing a target region and an inner surface opposite to the outer surface;
a cover body coupled to the housing defining a space inside the housing and cover an upper portion of the housing;
an irradiation opening disposed on the housing facing the target region;
a light source disposed on a substrate in the housing and configured to emit light toward the target region through the irradiation opening;
a power supply configured to supply power to the light source to turn on the light source; and
a charging terminal electrically connected to the power supply and providing a path through which power is supplied from an external power source to charge the power supply,
wherein the light source includes light emitting elements and the light emitting elements are disposed on the substrate to be spaced apart from one another by a predetermined interval such that a surface of a target in the target region is evenly irradiated with the light emitted by the light emitting elements,
wherein the light emitting elements comprises a first light emitting element and a second light emitting element,
wherein the first light emitting element and the second light emitting element have different peak wavelengths from each other, and
wherein the irradiation opening has a diameter allowing at least 50% of the light emitted from the light source to pass therethrough.

12. The sterilizing device of claim 11, further comprising:
a controller electrically coupled to the power supply and configured to control a power supply time of the power supply according to a present period of time.

13. The sterilizing device of claim 11, wherein the first light emitting element and the second light emitting element are configured to be simultaneously turned on.

14. The sterilizing device of claim 11, wherein the irradiation opening has an irradiation opening-enlarged portion having a cross-section gradually widening along a direction away from the light source.

15. The sterilizing device of claim 14, wherein the irradiation opening-enlarged portion has a curved shape or a tapered shape.

16. The sterilizing device of claim 11, wherein the first light emitting element has a peak wavelength to inactivate at least one pathogen included in the target.

17. The sterilizing device of claim 11, wherein the second light emitting element has a peak wavelength in a visible range and disposed near the first light emitting element.

18. The sterilizing device of claim 11, wherein the light source is configured to emit the light at a dose between 5 mJ/cm$^2$ and 20 mJ/cm$^2$ to inactivate a pathogen including *E. coli* that is included in the target within the target region.

19. The sterilizing device of claim 11, wherein the light source is configured to emit the light at a dose between 7 mJ/cm$^2$ and 20 mJ/cm$^2$ to inactivate a pathogen including *Staphylococcus aureus* that is included in the target within the target region.

20. The sterilizing device of claim 11, further comprising;
a reflector disposed on the cover body and including a material having a reflectivity to reflect the light emitted from the light source.

* * * * *